United States Patent
Wu et al.

(10) Patent No.: US 12,152,057 B2
(45) Date of Patent: *Nov. 26, 2024

(54) FUSION PROTEINS FOR INHIBITING ANGIOGENESIS

(71) Applicant: Allgenesis Biotherapeutics Inc., Taipei (TW)

(72) Inventors: Pei-tzu Wu, Taipei (TW); Jia-Hau Shiu, Taipei (TW); Madhu Cherukury, Irvine, CA (US); Tan Nguyen, Fullerton, CA (US); Kevin Zen, Del Mar, CA (US)

(73) Assignee: Allgenesis Biotherapeutics Inc., Taipei (TW)

( * ) Notice: Subject to any disclaimer, the term of this patent is extended or adjusted under 35 U.S.C. 154(b) by 175 days.

This patent is subject to a terminal disclaimer.

(21) Appl. No.: 16/803,561

(22) Filed: Feb. 27, 2020

(65) Prior Publication Data

US 2020/0181214 A1 Jun. 11, 2020

Related U.S. Application Data

(63) Continuation of application No. 15/739,089, filed as application No. PCT/IB2016/053794 on Jun. 24, 2016, now abandoned.

(Continued)

(51) Int. Cl.
*A61K 39/00* (2006.01)
*A61K 38/00* (2006.01)
(Continued)

(52) U.S. Cl.
CPC .............. *C07K 14/46* (2013.01); *A61K 38/00* (2013.01); *A61P 9/10* (2018.01); *C07K 14/71* (2013.01);
(Continued)

(58) Field of Classification Search
None
See application file for complete search history.

(56) References Cited

U.S. PATENT DOCUMENTS 7,750,138 B2 7/2010 Fang et al.
7,943,728 B2 5/2011 Chuang et al.
(Continued)

FOREIGN PATENT DOCUMENTS

WO 2007134876 11/2007
WO 2007134876 A2 11/2007
(Continued)

OTHER PUBLICATIONS

Kluza et al. Synergistic Targeting of αvβ3 Integrin and Galectin-1 with Heteromultivalent Paramagnetic Liposomes for Combined MR Imaging and Treatment of Angiogenesis. Nano Lett. 2010, 10, 52-58. (Year: 2010).*

(Continued)

*Primary Examiner* — Maher M Haddad
(74) *Attorney, Agent, or Firm* — Ice Miller, LLP

(57) ABSTRACT

The present invention relates to a biologic that inhibits angiogenesis. In particular, the present invention relates to fusion proteins that inhibit the integrin activated pathway and one other angiogenic factor-activated pathway, the compositions of these fusion proteins, as well as methods for producing and using the same.

7 Claims, 5 Drawing Sheets

Specification includes a Sequence Listing.

Related U.S. Application Data

(60) Provisional application No. 62/185,716, filed on Jun. 28, 2015.

(51) Int. Cl.
    *A61P 9/10*       (2006.01)
    *C07K 14/00*     (2006.01)
    *C07K 14/46*     (2006.01)
    *C07K 14/71*     (2006.01)

(52) U.S. Cl.
    CPC ...... *C07K 2319/00* (2013.01); *C07K 2319/02* (2013.01); *C07K 2319/30* (2013.01)

(56) References Cited

U.S. PATENT DOCUMENTS

| | | |
|---|---|---|
| 9,044,436 B2 | 6/2015 | Chuang et al. |
| 9,988,611 B2 | 6/2018 | Her et al. |
| 10,508,137 B2 | 12/2019 | Chuang |
| 2003/0027751 A1 | 2/2003 | Kovesdi et al. |
| 2003/0064053 A1 | 4/2003 | Liu et al. |
| 2006/0040325 A1 | 2/2006 | Wu et al. |
| 2006/0177443 A1 | 8/2006 | Fanslow, III et al. |
| 2006/0234347 A1* | 10/2006 | Harding ............. C07K 14/71 435/456 |
| 2008/0188413 A1 | 8/2008 | Chuang et al. |
| 2008/0207502 A1 | 8/2008 | Rastelli et al. |
| 2013/0303733 A1 | 11/2013 | Barbas |
| 2014/0213769 A1 | 7/2014 | Hong et al. |
| 2015/0079084 A1 | 3/2015 | Her et al. |
| 2015/0266942 A1 | 9/2015 | Tian et al. |
| 2015/0266945 A1 | 9/2015 | Lai |
| 2017/0267731 A1 | 9/2017 | Chuang et al. |
| 2017/0369552 A1* | 12/2017 | Zen .................... A61P 27/02 |

FOREIGN PATENT DOCUMENTS

| | | |
|---|---|---|
| WO | 2014160507 A1 | 10/2014 |
| WO | 2017001990 A1 | 1/2017 |

OTHER PUBLICATIONS

Kwan et al. Tumor vasculature targeting for improving solid tumor delivery of cancer therapeutics. Protein Science, ( 2012) vol. 21, Supp. 1, pp. 114. Abs No. 155. (Year: 2012).*

Jiang Peiru. Design of Integrin α5β1-specific Disintegrin Using Rhodostomin as the Scaffold. National Cheng Kung University. Institute of Biochemistry and Molecular Biology. Doctoral thesis, Jul. 21, 2009. Abstract. (Year: 2009).*

Michael, Iacovos & Sung, Hoon-Ki & Nagy, Andras. (2011). Abstract 1387: Development of novel antiangiogenic biologics: multifunctional VEGF traps. Cancer Research. 70. 1387-1387. 10.1158/1538-7445.AM10-1387. (Year: 2011).*

Michael, Iacovos P., Development of novel antiangiogenic biologics. Ph.D thesis. University of Toronto, 2011, pp. 1-219. (Year: 2011).*

Cochran et al. Engineered bispecific proteins that simultaneously bind to and inhibit both VEGFR2 and alphav beta3 integrin for cancer therapy and diagnosis. Protein Science, (Aug. 2010) vol. 19, Supp. 1, pp. 199-200. Abstract#: 404. (Year: 2010).*

Lu et al. Antiangiogenic and antitumor activity of 6-(2-aminoethyl) amino-5-chlorouracil, a novel small molecule inhibitor of thymidine phosphorylase, in combination with the vascular endothelial growth factor-trap. Clin. Cancer Res., 15 (2009), pp. 5136-5144. (Year: 2009).*

Le et al. Specific blockade of VEGF and HER2 pathways results in greater growth inhibition of breast cancer xenografts that overexpress HER2. Cell Cycle, 7 (2008), pp. 3747-3758. (Year: 2008).*

Hu et al. Vascular endothelial growth factor trap combined with paclitaxel strikingly inhibits tumor and ascites, prolonging survival in a human ovarian cancer model. Clin. Cancer Res., 11 (2005), pp. 6966-6971. (Year: 2005).*

Harb et al. Outcomes of Combination Therapy using Aflibercept and Dexamethasone Intravitreal Implant versus Dexamethasone Monotherapy for Macular Edema Secondary to Retinal Vein Occlusion. Middle East Afr J Ophthalmol. Jan.-Mar. 2021; 28(1): 18-22. (Year: 2021).*

Int'l Preliminary Report on Patentability issued Jan. 2, 2018 in Int'l Application PCT/IB2016/053794.

Jing et al., "Abstract 1385: Fusion Protein containing RGD-endostatin and human Fc of IgG4 improves anti-angiogenic and anti-tumor activity", Cancer Research, 70, 2010 (Abstract).

Wu et al., "Dual Function of RGD-Modified VEGI-192 for Breast Cancer Treatment", Bioconjugate Chemistry, 23, pp. 786-804, 2012.

Holash et al., "VEGF-Trap: A VEGF blocker with potent antitumor effects", PNAS, vol. 99, No. 17, pp. 11393-11398, 2002.

Huang et al. Viper Venom Components Affecting Angiogenesis. Haemostasis 2001;31:192-206. (Year: 2001).

Shiu et al. Effect of P to A Mutation of the N-Terminal Residue Adjacent to the Rgd Motif on Rhodostomin: Importance of Dynamics in Integrin Recognition. PLoS ONE 7(1): e28833. (Year: 2012).

Chen et al. Effect of D to E mutation of the RGD motif in rhodostomin on its activity, structure, and dynamics: Importance of the interactions between the D residue and integrin. Proteins 2009; 76:808-821. (Year: 2009).

Kolvunen et al. Phage Libraries Displaying Cyclic Peptides with Different Ring Sizes: Ligand Specificities of the ROD-Directed Integrins. Biotechnology (NY). Mar. 1995;13(3):265-70. (Year: 1995).

Lu et al. Preferential antagonism of the interactions of the integrin a(IIb)ß3 with immobilized glycoprotein ligands by snake-venom RGD (Arg-Gly-Asp) proteins. Evidence supporting a functional role . . . Biochemical Journal 304 (Pt 3):929-36. (Year: 1994).

Kuntz ID., Structure-Based Strategies for Drug Design and Discovery. Science 257:1078-1082 (Year: 1992).

Miller and Dill., Ligand binding to proteins: the binding landscape model. Protein Sci. Oct. 1997; 6(10): 2166-2179. (Year: 1997).

Koivuen et al. Identification of Receptor Ligands with Phage Display Peptide Libraries. J Nuc A Med; 40:883-888 (Year: 1999).

Patel S., Combination therapy for age-related macular degeneration. Retina 29:S45-S48 (Year: 2009).

Emerson et al. Current and emerging therapies for the treatment of age-related macular degeneration. Clin. Ophthal., 2(2): 377-388 (Year: 2008).

International Search Report and Written Opinion issued Dec. 16, 2016 from International Application No. PCT/IB2016/053794.

Dorrell et al. Combination angiostatic therapy completely inhibits ocular and tumor angiogenesis. Proceedings of the National Academy of Sciences Jan. 2007, 104 (3) 967-972. (Year: 2007).

Lee et al. Abstract 2327: Anti-angiogenic activity of a CovX bi-functional antibody conjugate targeting both activin-receptor like kinase type 1 (ALK-1) and vascular endothelial growth factor (VEGF). Cancer Res Apr. 15, 2012 (72) (8 Supplement) 2327; DOI: 10.1158/1538-7445.AM2012-2327 (Year: 2012) (4 pages).

Yao-Tsung Chang abstract (Doctoral Thesis. Structure-activity relationships of the RGD loop, linker region, and C-terminus of Rhodostomin mutants in the recognition of integrins. , Jan. 1, 2014) (Year: 2014) (13 pages).

* cited by examiner

FUSION PROTEINS FOR INHIBITING ANGIOGENESIS

CROSS-REFERENCE TO RELATED APPLICATIONS

This application is a continuation application of U.S. patent application Ser. No. 15/739,089 filed Dec. 21, 2017, which is a 371 of International Application No. PCT/IB2016/053794 filed Jun. 24, 2016, which claims the benefit of U.S. Provisional Application No. 62/185,716 filed Jun. 28, 2015, the disclosures of which are incorporated herein by reference in their entirety.

FIELD OF THE INVENTION

The present invention relates to a biologic that inhibits angiogenesis. In particular, the present invention relates to fusion proteins that inhibit angiogenic factor-activated pathways, the compositions of these fusion proteins, as well as methods for producing and using the same.

REFERENCE TO A SEQUENCE LISTING SUBMITTED AS A TEXT FILE VIA EFS WEB

The official copy of the sequence listing is submitted electronically via EFS-Web as an ASCII formatted sequence listing with a file named 688947_20U2_Sequence_Listing.txt, created on Feb. 18, 2020, and having a size of 37 kb, and is filed concurrently with the specification. The sequence listing contained in this ASCII formatted document is part of the specification and is herein incorporated by reference in its entirety.

BACKGROUND OF THE INVENTION

Angiogenesis is the process of growing new blood vessels from the existing vasculature. It plays an important role in several physiological processes, including embryonic development, as well as tissue and wound repair (Folkman J et al., Angiogenic factors. Science 1987; 235:442-7). The physiologic steps of angiogenesis are well characterized, and involve proteolysis of the extracellular matrix, proliferation, migration, and assembly of the endothelial cells into a tubular channel, mural cell recruitment and differentiation, and extracellular matrix production (Carmeliet P et al., Nature. 2011; 473:298-307). Pathologic angiogenesis may occur in tumor formation, ocular disorders (e.g., diabetic retinopathy, diabetic macular edema or macular degeneration) arthritis, psoriasis, fibrotic diseases, inflammatory diseases, and arteriosclerosis (Polverini P J. Crit Rev Oral Biol Med. 1995; 6(3):230-47).

Pathologic angiogenesis is more heterogeneous and chaotic, often demonstrating tortuous vessel organization, hypoxic voids of various sizes, uneven and imperfect vessel walls and linings, and ineffective perfusion (Jain R K., Nat Med. 2003; 9(6):685-93). These distinct characteristics of new blood vessel formation in diseases have made therapeutic targeting of angiogenesis a challenge. Although anti-VEGF therapies such as Lucentis®, Eylea®, or off-label use of Avastin® can generally stabilize or improve visual function, sub-retinal scarring (fibrosis) can develop in approximately half of all treated eyes within two years after anti-VEGF treatment and has been identified as one cause of unsuccessful outcomes (Daniel E et al., Ophthalmology. 2014; 121(3):656-66). Many of the critical players in sub-retinal fibrosis are likely to be the growth factors and the matricellular proteins that are involved in the fibrotic process (cell proliferation, migration and ECM remodeling). Despite its complexity, with our increasing knowledge of the angiogenic process, anti-angiogenic drug development remains an area of great interest.

Currently, many key players in the neovascularization process have been identified, and the vascular endothelial growth factor (VEGF) family has a predominant role. The human VEGF family consists of 6 members: VEGF-A VEGF-B, VEGF-C, VEGF-D, VEGF-E, and placental growth factor (PlGF). In addition, multiple isoforms of VEGF-A, VEGF-B, and PlGF are generated through alternative RNA splicing (Sullivan et al., MAbs, 2002, 2(2): 165-75). VEGF-A is the primary factor involved with angiogenesis; it binds to both VEGFR-1 and VEGFR-2. The strategy of inhibiting angiogenesis by obstructing VEGF-A signaling has established successful therapies for treatment of specific cancers as well as retinal neovacular and ischemic diseases. (Major et al., J Pharmacol Exp Ther., 1997, 283(1):402-10; Willet et al., Nat. Med. 2004, 10:145-7; Papadopoulos et al., Angiogenesis, 2012, 15(2):171-85; Aiello et al., PNAS, 1995, 92:10457-61).

Other growth factors, cytokines, chemokines include Platelet Derived Growth Factors (PDGFs), Transforming Growth Factors beta (TGF-β), Epidermal Growth Factors (EGFs), Nerve Growth Factors (NGFs), Hypoxia-Induced Factor (HIF), Connective-Tissue Growth Factor (CTGF), Granulocyte-Macrophage Colony-Stimulating Factor (GM-CSF), Insulin-Like Growth Factor (IGF), Hepatocyte Growth Factors/Scatter Factor (HGF/SF), Tumor Necrosis Factor alpha (TNF-α), Interleukin 1 (IL-1), Interleukin 6 (IL-6), Interleukin 8 (IL-8), Interleukin 17 (IL-17), Interleukin 18 (IL-18), Interleukin 20 (IL-20), Interleukin 23 (IL-23), Chemoattractants such as C-C motif Ligand (CCL28, CCL21) and C-X-C motif Ligand (CXCL1, CXCL5), Macrophage migration Inhibitory Factor (MIF), and immune cell surface proteins such as Clusters of Differentiation (CDs). These factors are reported to be overexpressed and play key roles in angiogenesis-related diseases (Elshabrawy et al., Angiogenesis (2015) 18:433-448; Brian P. Eliceiri, Circ Res. 2001 Dec. 7; 89(12):1104-10). Targeting these factors to reduce their downstream pathway activation may decrease angiogenesis-related diseases.

Integrins, a family of cell surface receptors, are also found to be overexpressed on the endothelial cell surface and are believed to facilitate the growth and survival of newly forming vessels during angiogenesis. Integrins are heterodimeric cell surface receptors that interact with extracellular matrix proteins and are critical for many biological processes. The expression of integrins in various cell types are involved in tumor progression, and their ability to crosstalk with growth factor receptors has made them attractive therapeutic targets. (Staunton D E, et al., Adv Immunol. 2006; 91:111-57; Avraamides, C. J., et al., Nat Rev Cancer 2008; 8:604-617.) In particular, the integrin αvβ3 is upregulated in both tumor cells and angiogenic endothelial cells, and is important for tumor cell migration, angiogenesis, and dysregulated cell signaling. Therefore, antagonists of the integrin αvβ3 are intensively studied for their anti-angiogenic and anti-tumor properties (Desgrosellier J S et al., Nat Rev Cancer. 2010 10:9-22).

Disintegrins are the peptides found in snake venom of the viper family and mainly inhibit the function of β1- and β-associated integrins. They were first identified as inhibitors of integrin αIIbβ3 and were subsequently shown to bind with high affinity to other integrins, blocking the interaction of integrins with RGD-containing proteins. They contain 47 to 84 amino acids with about 4 to 7 disulfide bonds and carry the same RGD motif (McLane M A, et al., Proc Soc Exp Biol Med 1998 219: 109-119; Niewiarowski S, et al., Semin Hematol 1994 31: 289-300; Calvete J J., Curr Pharm Des. 2005 11: 829-835; Blobel C P et al., Curr Opin Cell Biol 1992 4: 760-765). The conserved RGD sequence in the disintegrin family plays the most important role in recognizing the integrins. Disintegrins were found to interact with eight out of twenty-four integrins and inhibited integrin-mediated cell adhesion, migration, and angiogenesis (McLane M A, et al., Front Biosci. 2008 13: 6617-6637; Swenson S, et al., Curr Pharm Des. 2007 13: 2860-2871). Animal studies showed that disintegrins targeted neovascular endothelium and metastatic tumors, indicating their potential use in cancer therapy. The specific binding of RGD-containing proteins to integrin is a function of both the conformation and the local sequence surrounding the RGD motif. Many studies have shown that the residues flanking the RGD motif of RGD-containing proteins affect their binding specificities and affinities to integrins (Scarborough R M et al., J Biol Chem 1993 268: 1058-1065; Rahman S et al., Biochem J 1998 335: 247-257).

Angiogenesis is a complex biological process which involves various growth factors and signaling receptors, and targeting single molecules in the signaling cascade may not provide an effective clinical treatment for uncontrolled angiogenesis in diseases such as cancer. Therefore, there is a growing need to develop innovative therapeutics capable of binding several key angiogenic factors in a cooperative manner to effectively inhibit angiogenesis and progression of the disease.

BRIEF SUMMARY OF THE INVENTION

The invention provided herein discloses polypeptides for specifically binding to multiple targets so as to antagonize several angiogenic factors. The invention also provides fusion proteins that inhibit a selective integrin pathway and other angiogenic pathways. The invention further provides compositions having these fusion proteins. The invention further provides compositions having a vector that comprises a nucleic acid encoding the fusion proteins. The invention further describes methods for producing and using these fusion proteins for the treatment or prevention of angiogenic diseases, ocular diseases, autoimmune diseases, inflammatory diseases, fibrotic diseases, and/or cancer.

In accordance with the present invention, a fusion protein comprising an integrin binding peptide selected from a group consisting of disintegrin, anti-integrin $\alpha v\beta x$ antibody, anti-integrin $\alpha 5\beta 1$ antibody, fibronectin targeting integrin $\alpha v\beta x$ or $\alpha 5\beta 1$ and their integrin binding fragments, other protein binding peptide targeting an angiogenic factor and a Fc domain, wherein x is 1, 3, 5, 6 or 8. In some embodiments, the angiogenic factor comprises Angiopoietin (ANG), Ephrin (Eph), Fibroblast Growth Factor (FGF), Neuropilin (NRP), Plasminogen Activators, Platelet-Derived Growth Factor (PDGF), Tumor Growth Factor beta (TGF-$\beta$), Vascular Endothelial Growth Factor (VEGF), Vascular Endothelial cadherin (VE-cadherin), Epidermal Growth Factors (EGFs), Nerve Growth Factors (NGFs), Connective-Tissue Growth Factor (CTGF), Granulocyte Macrophage Colony-Stimulating Factor (GM-CSF), Insulin-like Growth Factor (IGF), Hepatocyte Growth Factors/Scatter Factor (HGF/SF), Tumor Necrosis Factor alpha (TNF-$\alpha$), Interleukin 1 (IL-1), Interleukin 6 (IL-6), Interleukin 8 (IL-8), Interleukin 17 (IL-17), Interleukin 18 (IL-18), Interleukin 20 (IL-20), Interleukin 23 (IL-23), Chemoattractants such as C-C motif Ligand (CCL28, CCL21), C-X-C motif Ligand (CXCL1, CXCL5), Macrophage migration Inhibitory Factor (MIF), immune cell surface protein such as Clusters of Differentiation (CDs), and receptors thereof.

According to one aspect, the invention provides a fusion protein comprising an integrin binding peptide having an amino acid sequence selected from a group consisting of SEQ ID NO: 1, SEQ ID NO: 2, SEQ ID NO: 3, SEQ ID NO: 4, SEQ ID NO: 5, SEQ ID NO: 6, and SEQ ID NO: 7, or amino acid sequence having at least 85% sequence identity to SEQ ID NO: 1, SEQ ID NO: 2, SEQ ID NO: 3, SEQ ID NO: 4, SEQ ID NO: 5, SEQ ID NO: 6, and SEQ ID NO: 7, other protein binding peptide comprising extracellular domains of VEGF receptors, and a Fc domain, wherein the integrin binding peptide has at least one mutation on or adjacent to a RGD motif.

According to another aspect, the invention provides a fusion protein comprising an integrin binding peptide that includes disintegrin and its integrin binding fragments, other protein binding peptide comprising extracellular domains of VEGF receptors and a Fc domain, wherein the integrin binding peptide comprises at least one mutation on or adjacent to the RGD motif. In some embodiments, the fusion protein comprises the integrin binding peptide, the Fc domain, and the other protein binding peptide from C-terminus to N-terminus. In some embodiments, the fusion protein comprises the integrin binding peptide, the Fc domain, and the other protein binding peptide from N-terminus to C-terminus. In further embodiments of the fusion protein, the integrin binding peptide has at least 85% sequence identity to SEQ ID NO: 1, SEQ ID NO: 2, SEQ ID NO: 3, SEQ ID NO: 4, SEQ ID NO: 5, SEQ ID NO: 6 or SEQ ID NO: 7.

In accordance with other embodiments, the invention also provides a fusion protein comprising an integrin binding peptide that includes an amino acid sequence of SEQ ID NO:1 with at least one mutation on or adjacent to the RGD motif, an amino acid sequence having at least 85% sequence identity to SEQ ID NO: 1 or an amino acid sequence of SEQ ID NO: 2, a human or humanized constant sub-region comprising an immunoglobulin CH2 domain and a CH3 domain, and other protein binding peptide having an Ig-like domain D2 of a VEGFR1 and an Ig-like domain D3 of a VEGFR2. In a further embodiment of the fusion protein, the integrin binding peptide has at least 85% sequence identity to SEQ ID NO: 2.

In accordance with one aspect, the invention provides a nucleic acid sequence encoding a fusion protein of the invention disclosed herein.

In accordance with another aspect, the invention provides a dimer of fusion proteins of the invention disclosed herein.

In accordance with another aspect, the invention provides a method of producing a fusion protein of the invention, comprising culturing a host cell transfected with a vector comprising a nucleic acid sequence of the invention, under a condition that produces the fusion protein and recovering the fusion protein produced by the host cell.

In accordance with another aspect, the invention provides a method of treating or preventing an angiogenic disease comprising administering an effective amount of the fusion protein to a subject in need thereof. In some embodiments, the angiogenic disease comprises rheumatoid arthritis, inflammatory arthritis, osteoarthritis, ocular and systemic cancer, tumor related metastasis and invasion, systemic fibrotic diseases including idiopathic lung fibrosis (IPF), nonalcoholic steatohepatitis (NASH) or liver fibrosis, diabetic nephropathy and/or kidney fibrosis, dermal fibrosis or keloid, wound healing, cardio-fibrosis, and ischemia-induced stroke; ocular disease characterized by neovascularization or ischemia (such as choroidal neovascularization), uveitis, retinitis pigmentosa, age-related macular degeneration (AMD), diabetic retinopathy and diabetic macular edema (DME), central and branch retinal vein occlusion (CRVO and BRVO), human retinopathy of prematurity (ROP), polypoidal choroidal vasculopathy (PCV), symptomatic vitreomacular adhesion, and glaucoma. In some embodiments, the fusion protein of the invention comprises a linker sequence between the integrin binding peptide and the other protein binding peptide. In some embodiments, the fusion protein of the invention comprises the signal peptide sequence upstream of the other binding domain.

In accordance with another aspect, the invention provides a composition comprising a fusion protein of the invention and a pharmaceutically acceptable carrier.

In accordance with another aspect, the invention provides a polypeptide targeting to multiple angiogenic factors comprising: an integrin binding peptide comprising an amino acid sequence selected from a group consisting of SEQ ID NO: 1, SEQ ID NO: 2, SEQ ID NO: 3, SEQ ID NO: 4, SEQ ID NO: 5, SEQ ID NO: 6, and SEQ ID NO: 7, or amino acid sequence having at least 85% sequence identity to SEQ ID NO: 1, SEQ ID NO: 2, SEQ ID NO: 3, SEQ ID NO: 4, SEQ ID NO: 5, SEQ ID NO: 6, and SEQ ID NO: 7; other protein binding peptide selected from a group consisting of extracellular domains of VEGF receptors, anti-VEGF antibody, anti-PDGF antibody and their fragments; and a Fc domain; wherein the integrin binding peptide comprising at least one mutation on or adjacent to the RGD motif.

In some embodiments, the extracellular domains of VEGF receptors in the polypeptide of the invention comprise the Ig-like domains D1-D7 of the VEGF receptors. In some embodiments, the extracellular domains of VEGF receptors in the polypeptide of the invention comprise: i) the Ig-like domain 2 (D2) of a VEGFR1 and an Ig-like domain 3 (D3) of a VEGFR2; ii) the amino acid sequence of SED ID NO: 10; or iii) an amino acid sequence having at least 90% identity to SEQ ID NO: 10. In some embodiments, the extracellular domains of PDGF receptors in the polypeptide of the invention comprise the Ig-like domains 1-5 of the PDGF receptors. In some embodiments, the extracellular domains of PDGF receptors in the polypeptide of the invention comprise: i) the Ig-like domains 1-3 of a PDGFRβ; ii) the amino acid sequence of SED ID NO: 11; or iii) an amino acid sequence having at least 90% identity to SEQ ID NO: 11. In some embodiments, the polypeptide of the invention further comprises a Gly-Ser (GS) or Gly-Gly-Gly-Gly-Gly-Gly-Gly-Gly-Gly ($G_9$) linker between the Fc domain and the integrin binding peptide or the extracellular domains of VEGF or PDGF receptors.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents and patent applications cited herein are hereby incorporated by reference in their entirety for all purposes.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings.

DESCRIPTION OF THE INVENTION

Figure 1:
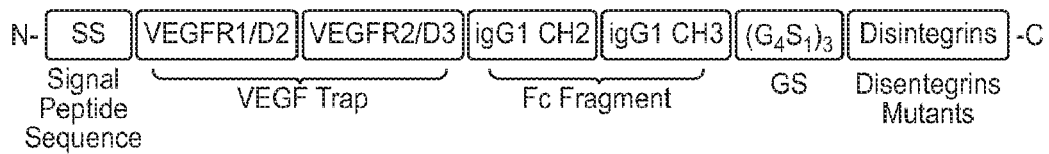
FIG. 1 is a schematic illustrating the composition of an exemplary fusion protein according to one embodiment of the invention.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a binding domain" includes a plurality of binding domains and equivalents thereof known to those skilled in the art.

As used herein, the term "polypeptide" and "protein" may be used interchangeably to refer to a long chain of peptide having an amino acid sequence of the native protein or the amino acid sequence with one or more mutations such as deletion, additions, and/or substitutions of one or more amino acid residues.

A "fusion protein" refers to a protein having two or more portions covalently linked together, where each of the portions is derived from different proteins.

The present invention provides a fusion protein comprising an integrin binding peptide selected from a group consisting of disintegrin (see U.S. Pat. No. 7,943,728 and PCT Application No. PCT/US 15/46322 for the description of amino acid sequences, each of which is incorporated by reference in its entirety), anti-integrin αvβx antibody (see U.S. Pat. Nos. 6,160,099 and 8,350,010 for the description of amino acid sequences, each of which is incorporated by reference in its entirety), anti-integrin α5β1 antibody, fibronectin (see U.S. Pub. No. 2015/0218251 for the description of amino acid sequences, which is incorporated by reference in its entirety) targeting integrin isoform αvβx or α5β1 and their integrin binding fragments, other protein binding peptide targeting an angiogenic factor and a Fc domain, wherein x is 1, 3, 5, 6 or 8.

The term "antibody", as used herein, is intended to refer to immunoglobulin molecules comprised of four polypeptide chains, two heavy chains and two light chains interconnected by disulfide bonds. A full-length heavy chain includes a variable region domain, VH, and three constant region domains, CH1, CH2 and CH3. The VH domain is at the amino-terminus of the polypeptide, and the CH3 domain is at the carboxy-terminus. A full-length light chain includes a variable region domain, VL, and a constant region domain, CL. An antigen binding fragment (Fab) is comprised of one light chain and the CH1 and variable regions of one heavy chain. The heavy chain of a Fab molecule cannot form a disulfide bond with another heavy chain molecule. A Fab' fragment contains one light chain and one heavy chain that contains more of the constant region, between the CH1 and CH2 domains, such that an interchain disulfide bond can be formed between two heavy chains to form diabodies. A variable fragment (Fv) region comprises the variable regions from both the heavy and light chains, but lacks the constant regions. Single-chain fragments (scFv) are Fv molecules in which the heavy and light chain variable regions have been connected by a flexible linker to form a single polypeptide chain which forms an antigen-binding region. Single chain antibodies are discussed in detail in WO88/01649 and U.S. Pat. Nos. 4,946,778 and 5,260,203. As used herein, the term "antibody" includes the an immunoglobulin molecule with two full length L-chains and two full length H-chains, and fragments thereof, such as an antigen binding fragment (Fab), a Fv region, a scFv, etc.

The term "Fc domain" refers to a molecule or sequence comprising the sequence of a non-antigen binding portion of an antibody, whether in monomeric or multimeric form. The original immunoglobulin source of an Fc is preferably of human origin and can be from any isotype, e.g., IgG, IgA, IgM, IgE or IgD. A full-length Fc consists of the following Ig heavy chain regions: CH1, CH2 and CH3, wherein the CH1 and CH2 regions are typically connected by a flexible hinge region.

The present invention provides a fusion protein comprising an integrin binding peptide that includes disintegrin and its integrin binding fragments, other protein binding peptide comprising extracellular domains of VEGF receptor and a Fc domain, wherein the integrin binding peptide comprises at least one mutation on or adjacent to the RGD motif. In accordance with embodiments of the present invention, the disintegrin and its integrin binding fragments have an amino acid sequence selected from a group consisting of SEQ ID NO: 1, SEQ ID NO: 2, SEQ ID NO: 3, SEQ ID NO: 4, SEQ ID NO: 5, SEQ ID NO: 6, and SEQ ID NO: 7, or amino acid sequence having at least 85% sequence identity to SEQ ID NO: 1, SEQ ID NO: 2, SEQ ID NO: 3, SEQ ID NO: 4, SEQ ID NO: 5, SEQ ID NO: 6, and SEQ ID NO: 7

As used herein, "disintegrin" refers to a class of cysteine-rich proteins or polypeptides that are potent soluble ligands of integrins. The RGD motif is a tri-peptide (Arg-Gly-Asp) conserved in most of monomeric disintegrins and is located at an integrin-binding loop. The disintegrins described herein are isolated from snake venom or derived from wild-type forms and have at least one mutation on or adjacent to a RGD motif to selectively bind to or target to various integrin isoforms. The term "adjacent to a RGD motif" as used herein means any mutation which occurs at any amino acid residue within 15-20 amino acids from the RGD motif in a given peptide or polypeptide sequence.

Other amino acid sequence variants of the disintegrin are also contemplated. For example, binding affinity and/or other biological properties of a disintegrin can be improved by altering the amino acid sequence encoding the protein. Disintegrin mutants can be prepared by introducing appropriate modifications into the nucleic acid sequence encoding the protein or by introducing modification by peptide synthesis. Such modifications include mutations such as deletions from, insertions into, and/or substitutions within the nucleic or amino acid sequence of the disintegrin. Any combination of deletion, insertion, and substitution can be made to arrive at the final amino acid construct of the disintegrin provided that the final construct possesses the desired characteristics such as binding to an integrin superfamily member and/or inhibiting the integrin activated pathway.

Substantial modifications in the biological properties of the proteins or polypeptides are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

A useful method for identifying certain residues or regions of the fusion protein that are preferred locations for mutagenesis is known as "alanine scanning mutagenesis" as described in Science, 1989, 244:1081-1085. For example, a residue or group of target residues are identified (e.g., charged residues such as Arg, Asp, His, Lys and Glu) and replaced by a neutral or negatively charged amino acid (most preferably alanine or polyalanine) to affect the interaction of the amino acids with the target binding partner. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, random mutagenesis may be conducted at the target codon or region and the expressed fusion polypeptide variants are screened for desired activity. For example, cysteine bond(s) may be added to the fusion protein or protein components to improve its stability.

Accordingly, provided herein are disintegrin mutants that can be a component of any fusion protein disclosed herein. In some embodiments, the disintegrin comprises an amino acid sequence with at least 85%, at least 90%, at least 95%, or at least 99% sequence identity to the amino acid sequence of disintegrins selected from a group consisting of Rhodostomin (SEQ ID NO: 1), Triflavin (SEQ ID NO: 3), Echistatin (SEQ ID NO: 4), Trimucrin (SEQ ID NO: 5), Elegantin (SEQ ID NO: 6) and Trigramin (SEQ ID NO: 7). In some embodiments, a disintegrin comprises an amino acid sequence having at least one mutation on or adjacent to the RGD motif of Rhodostomin (SEQ ID NO: 1), Triflavin (SEQ ID NO: 3), Echistatin (SEQ ID NO: 4), Trimucrin (SEQ ID NO: 5), Elegantin (SEQ ID NO: 6) or Trigramin (SEQ ID NO: 7). In some embodiments, the disintegrin comprises an amino acid sequence with at least 85%, at least 90%, at least 95%, or at least 99% sequence identity to the amino acid sequence of a disintegrin mutant (SEQ ID NO: 2). The Xaa in SEQ ID NO: 2 indicates various positions that can be modified by either insertion, substitution or deletion to produce amino acid sequence variants that are different from the wild type form of disintegrin. According to some examples, the Xaa at position 50 of SEQ ID NO: 2 which corresponds to glycine (Gly) in the RGD motif of wild type Rhodostomin (SEQ ID NO: 1) may be substituted with naturally occurring amino acids other than glycine to generate Rhodostomin mutants. In other examples, one or more Xaa in SEQ ID NO: 2 may also be substituted with naturally occurring amino acids other than those originally found in corresponding positions of wild type Rhodostomin (SEQ ID NO: 1) to generate various Rhodostomin mutants. It is further noted that the disintegrin mutants are not limited to include only single mutation at any Xaa in SEQ ID NO: 2, multiple mutations that occur at several locations of Xaa in SEQ ID NO: 2 or corresponding locations in other consensus sequences of disintegrin (such as SEQ ID NOs: 3-7) may also be encompassed by the scope of the invention.

Rhodostomin mutants have been described in U.S. Pat. No. 7,943,728 and PCT Application No. PCT/US 15/46322 and their sequences are incorporated herein by reference. For example, PCT/US15/46322 describes the disintegrin variant comprises a mutant RGD loop having the amino acid sequence selected from the group consisting of SEQ ID NO: 24 to SEQ ID NO: 26, and at least one of a mutant linker having the amino acid sequence selected from the group consisting of SEQ ID NO: 29 to SEQ ID NO: 41, and a mutant C-terminus having the amino acid sequence selected from the group consisting of SEQ ID NO: 42 to SEQ ID NO: 49. More preferably, the disintegrin variant comprises the mutant RGD loop, the mutant linker and the mutant C-terminus described herein.

Mutants of rhodostomin or disintegrins with one or more modifications in addition to the RGD motif, e.g., in the linker region or the C-terminus, exhibited the capability to selectively binding to αVβ3, αVβ5, αVβ6, α5β1 or αIIbβ. For example, Rho variants with the mutation in the linker region ($^{39}X^{40}X^{41}X^{42}X^{43}X$), in which the SRAGK (SEQ ID NO: 50) was replaced by KKKRT (SEQ ID NO: 51), KKART (SEQ ID NO: 52), MKKGT (SEQ ID NO: 53), IEEGT (SEQ ID NO: 54), LKEGT (SEQ ID NO: 55), AKKRT (SEQ ID NO: 56), KAKRT (SEQ ID NO: 57), KKART (SEQ ID NO: 58), KKKAT (SEQ ID NO: 59), KKKRA (SEQ ID NO: 60), KAKRA (SEQ ID NO: 61), and SKAGT (SEQ ID NO: 62) amino acids, had their highest effects on integrins in the following order: αIIbβ3 (~2-fold) >α5β1 (~5-fold)>αVβ3 (~14-fold).

Rho variants with the mutation in the C-terminal region ($^{66}X^{67}X^{68}X^{69}X^{70}X$), in which the RYH was replaced by RYH (SEQ ID NO: 63), RNGL (SEQ ID NO: 64), RGLYG (SEQ ID NO: 65), RGLY (SEQ ID NO: 66), RDLYG (SEQ ID NO: 67), RDLY (SEQ ID NO: 68), RNGLYG (SEQ ID NO: 69), and RNPWNG (SEQ ID NO: 70) amino acids, had their highest effects on integrins in the following order: αIIbβ (~13-fold)>αVβ5 (~8-fold)=αVβ6 (~8-fold)>αVβ3 (~4-fold)>α5β1 (~2-fold). Table 1 shows the sequences of SEQ ID NOs: 24 to 49 and their corresponding positions on SEQ ID NO: 1.

TABLE 1

| SEQ ID NO | Sequence | Position on SEQ ID NO: 1 |
|---|---|---|
| 24 | RIARGDNP | 46-53 |
| 25 | RRARGDNP | |
| 26 | ARGRGDNP | |
| 27 | ARGRGDDL | |
| 28 | ARARGDNP | |
| 29 | KKKRTIC | 39-45 |
| 30 | MKKGTIC | |
| 31 | IEEGTIC | |
| 32 | KGAGKIC | |
| 33 | LKEGTIC | |
| 34 | AKKRTIC | |

TABLE 1-continued

| SEQ ID NO | Sequence | Position on SEQ ID NO: 1 |
|---|---|---|
| 35 | KAKRTIC | |
| 36 | KKARTIC | |
| 37 | KKKATIC | |
| 38 | KKKRAIC | |
| 39 | KAKRAIC | |
| 40 | SKAGTIC | |
| 41 | KKKRTIC | |
| 42 | PRWNDL | 65-68 |
| 43 | PRNGLYG | |
| 44 | PGLYG | |
| 45 | PDLYG | |
| 46 | PPLYG | |
| 47 | PRLYG | |
| 48 | PELYG | |
| 49 | PYLYG | |

Although the variants of disintegrins are discussed mostly with reference to the amino acid sequences discussed above, polypeptide sequences or nucleotide sequence encoding the snake venom such as Albolabrin, Applagin, Basilicin, Batroxostatin, Bitistatin, Cereberin, Cerastin, Crotatroxin, Durissin, Flavoridin, Flavostatin, Halysin, Halystatin, Jararacin, Jarastatin, Kistrin, Lachesin, Lutosin, Molossin, Salmosin, Saxatilin, Tergeminin, Trimestatin, Trimutase, Ussuristatin, Viridian and their mutants having at least one mutation on or adjacent to the RGD motif may also be encompassed by the scope of the present invention.

Without being bound by theory, it is contemplated herein that disintegrins inhibit the integrin activated pathway by binding to an integrin superfamily member to block its interaction with a multivalent integrin receptor. In some aspects, the disintegrin binds to an integrin superfamily member which includes but is not limited to the integrin isoforms αvβ1, αvβ3, αvβ5, αvβ6, αvβ8, α5β1 and/or αvIIbβ3.

According to the present invention, the other protein binding peptide of the fusion protein may be receptor protein that binds to a target selected from the group consisting of a tumor antigen, a TNF receptor superfamily member, a Hedgehog family member, a receptor tyrosine kinase, a proteoglycan-related molecule, a TGF-beta superfamily member, a Wnt-related molecule and an angiogenesis target.

According to some embodiments of the invention, the other protein binding peptide may specifically bind to an angiogenesis target which includes but is not limited to Angiopoietin (ANG), Ephrin (Eph), Fibroblast Growth Factor (FGF), Neuropilin (NRP), Plasminogen Activators, Platelet-Derived Growth Factor (PDGF), Tumor Growth factor beta (TGF-β), Vascular Endothelial Growth Factor (VEGF), Vascular Endothelial cadherin (VE-cadherin) and their receptors. Therefore, in accordance with embodiments of the invention, the other protein binding peptide may include extracellular portions of a receptor protein that binds to and antagonizes the angiogenesis target. In other embodiments, the other protein binding peptide may bind to extracellular portions of angiogenic factor receptors.

In some embodiments, the other protein binding peptide may be an anti-VEGF antibody (see WO2015/200905 for the description of its amino acid sequence, which is incorporated herein by reference in its entirety) that binds to the VEGF ligand or an anti-VEGFR1 or anti-VEGFR2 antibody (see U.S. Pat. No. 5,874,542 for the description of its amino acid sequence, which is incorporated herein by reference in its entirety) that binds to VEGF receptor. In other embodiments, the other protein binding peptide may also be an anti-PDGF antibody (see U.S. Pat. No. 5,094,941 for the description of its amino acid sequence, which is incorporated herein by reference in its entirety) that binds to the PDGF ligand or an anti-PDGFR beta antibody (see U.S. Pat. No. 9,265,827 for the description of its amino acid sequence, which is incorporated herein by reference in its entirety for all purposes) that binds to PDGF receptor.

In certain embodiments, the other protein binding peptide binds to the same VEGF as any one of VEGF receptors (VEGFR): VEGFR1, VEGFR2 and VEGFR3. In some embodiments, the other protein binding peptide comprises at least one extracellular portion of a VEGFR of any of the VEGFRs described herein. For example, the other protein binding peptide comprises at least one extracellular portion of VEGFR1 or one extracellular portion of VEGFR2. In another example, the other protein binding peptide comprises one extracellular portion of VEGFR1 such as Ig-like domain 2 (D2) and one extracellular portion of VEGFR2 such as Ig-like domain 3 (D3). In some aspect, the other protein binding peptide comprises one extracellular portion of a VEGFR1 comprising amino acid sequence of SEQ ID NO: 8 and one extracellular portion of a VEGFR2 comprising amino acid sequence of SEQ ID NO: 9. In some aspect, the other protein binding peptide comprises a fusion of extracellular portions of VEGFR1 and VEGFR2 comprising an amino acid sequence of SEQ ID NO: 10 or an amino acid sequence with at least 85% sequence identity to SEQ ID NO: 10.

In other embodiments, the other protein binding peptide binds to the same PDGF as any one of PDGF receptors (PDGFR): PDGFR-α and PDGFR-β. In some embodiments, the other protein binding peptide comprises at least one extracellular portion of a PDGFR of any of the PDGFRs described herein. For example, the other protein binding peptide comprises at least one extracellular portion of PDGFR-α or one extracellular portion of PDGFR-β. In another example, the other protein binding peptide comprises one extracellular portion of PDGFR-β such as Ig-like domain 1-3. In some aspect, the other protein binding peptide comprises an extracellular portion of a PDGFR comprising an amino acid sequence of SEQ ID NO: 11 or an amino acid sequence with at least 85% sequence identity to SEQ ID NO: 11.

In accordance with other embodiments, the invention also provides a fusion protein comprising an integrin binding peptide that includes an amino acid sequence of SEQ ID NO:1 with at least one mutation on or adjacent to the RGD motif, an amino acid sequence having at least 85% sequence identity to SEQ ID NO: 1 or an amino acid sequence of SEQ ID NO: 2, a human or humanized constant sub-region comprising an immunoglobulin CH2 domain and a CH3 domain, and other protein binding peptide having an Ig-like D2 of a VEGFR1 and an Ig-like D3 of a VEGFR2. In a further embodiment of the fusion protein, the integrin binding peptide has at least 85% sequence identity to SEQ ID NO: 2.

The term "percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, as those described in Current Protocols in Molecular Biology (Ausubel et al., eds., 1987), and including BLAST, BLAST-2, ALIGN or Megalign (DNASTAR) Software. Those skilled in the art can determine appropriate parameters for measuring alignment, including any algorithms needed to achieve maximal alignment over the full length of the sequences being compared. For purposes herein, the % amino acid sequence identity of a given amino acid sequence A to, with or against a given amino acid sequence B is calculated as follows: 100 times the fraction X/Y, where X is the number of amino acid residues score as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The present invention provides a dimeric fusion protein comprising two fusion proteins, wherein each fusion protein comprises any fusion protein disclosed herein. In one embodiment, the dimeric fusion protein comprises two identical fusion proteins. In another embodiment, the dimeric fusion protein may comprise two different fusion proteins. The fusion proteins disclosed herein may form multimers of two or more identical fusion proteins or form heterologous fusion proteins through a multimerization domain which includes a constant sub-region of a human or humanized antibody. In some embodiments, the constant sub-region of a human or humanized antibody is selected from the group consisting of an IgG Fc region, IgA Fc region, IgM Fc region, IgD Fc region and IgE Fc region. In the further embodiment, the constant sub-region of a human or humanized antibody is selected from the group consisting of an IgG1 Fc region, IgG2 Fc region, IgG3 Fc region and IgG4 Fc region. In some aspect, the sub-region comprises a CH2 region and a CH3 region of IgG1, IgG2, IgG3, or IgG4. Amino acid sequences encoding immunoglobulins that comprise Fc regions are well known in the art.

The components of the fusion protein may be connected directly to each other or be connected via linkers. Generally, the term "linker" means one or more molecules e.g., nucleic acids, amino acids or non-peptide moieties which may be inserted between one or more component domains. For example, linkers may be used to provide a desirable site of interest between components for ease of manipulation. A linker may also be provided to enhance expression of the fusion protein from a host cell, to decrease steric hindrance such that the component may assume its optimal tertiary structure and/or interact appropriately with its target molecule. A linker sequence may include one or more amino acids naturally connected to a receptor component, or may be an added sequence used to enhance expression of the fusion protein, to provide specifically desired sites of interest, to allow component domains to form optimal tertiary structures and/or to enhance the interaction of a component with its target molecule.

Preferably, the linker increases flexibility of the fusion protein components without interfering with the structure of each functional component within the fusion protein. In some embodiments, the linker moiety is a peptide linker with a length of 2 to 100 amino acids. Exemplary linkers include linear peptides having at least two amino acid residues such as Gly-Gly, Gly-Ala-Gly, Gly-Pro-Ala, Gly (G)n and Gly-Ser (GS) linker. The GS linker described herein includes but is not limited to (GS)n, (GSGSG)n, $(G_2S)n$, $G_2S_2G$, $(G_2SG)n$, $(G_3S)n$, $(G_4S)n$, (GGSGG)nGn and $GSG_4SG_4SG$, wherein n is 1 or more. One example of the (G)n linker includes a $G_9$ linker. Suitable linear peptides include polyglycine, polyserine, polyproline, polyalanine and oligopeptides consisting of alanyl and/or serinyl and/or prolinyl and/or glycyl amino acid residues. The linker moieties may be used to link any of the components of the fusion proteins disclosed herein. In some embodiments, a linker is used between an extracellular portion of a receptor protein and a constant sub-region of an immunoglobulin. In other embodiments, a linker is used between disintegrin or its variant and a constant sub-region of an immunoglobulin. In certain embodiments, the fusion protein comprises a linker between an extracellular portion of a receptor protein and disintegrin or its variant, and a linker between disintegrin or its variant and a constant sub-region of an immunoglobulin. As embodied in the present invention, a fusion protein may comprise at least one linker but no more than four linkers.

The fusion protein described herein may or may not comprise a signal peptide that functions for secreting the fusion protein from a host cell. A nucleic acid sequence encoding the signal peptide can be operably linked to a nucleic acid sequence encoding the protein of interest. In some embodiments, the fusion protein comprises a signal peptide. In some embodiment, the fusion protein does not comprise a signal peptide.

Moreover, the fusion proteins described in the present invention may comprise modified forms of the protein binding peptides. For example, the fusion protein components may have post-translational modifications, including for example, glycosylation, sialylation, acetylation, and phosphorylation to any of the protein binding peptides.

Although the embodiments are generally described with reference to two protein binding peptides included in the fusion protein, the invention also contemplates a fusion protein which incorporates more than two protein binding peptides to provide any additional or synergistic effects in terms of inhibiting the process of angiogenesis. For example, there may be an additional protein binding peptide that binds to other angiogenesis targets or acts as angiogenic factor antagonists to be linked to the existing two protein binding peptides.

The present invention provides a nucleic acid encoding a fusion protein of the invention disclosed herein. The invention further provides a method of producing a fusion protein disclosed herein. The method involves culturing a host cell transfected with a vector which comprises a nucleic acid sequence of the invention and recovering the fusion protein produced by the host cell under suitable conditions.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine or pyrimidine bases, or other natural, chemically or biochemically modified, non-natural, or derivatized nucleotide bases.

Isolated nucleic acid molecules encoding a fusion protein or a component of a fusion protein can be in the form of RNA, such as mRNA, hnRNA, tRNA or any other form, or in the form of DNA, including, but not limited to cDNA and genomic DNA obtained by cloning or produced synthetically, or any combination thereof. The DNA can be triple-stranded, double-stranded or single-stranded, or any combination thereof. Any portion of at least one strand of the DNA or RNA can be the coding strand, known as the sense strand, or it can be the non-coding strand, also referred to as the anti-sense strand. The isolated nucleic acids encoding a fusion protein or fusion protein component can be prepared by a variety of methods known in the art including, but not limited to, isolation from a natural source or preparation by oligonucleotide-mediated mutagenesis, and cassette mutagenesis of an earlier prepared variant or a non-variant version of the fusion protein or fusion protein component. See *Molecular Cloning: A Laboratory Manual* (Sambrook et al., 4$^{th}$ ed., Cold Spring Harbor, N.Y. 2012) and *Current Protocols in Molecular Biology* (F. M. Ausubel, et al. eds., 2003).

A "vector" refers to a recombinant plasmid that comprises a nucleic acid to be delivered into a host cell, either in vitro or in vivo.

The present invention contemplates the use of a nucleic acid delivery vehicle for introduction of one or more nucleic acid sequences encoding a fusion protein or fusion protein component into a cell for expression of said protein. Examples of nucleic acid delivery vehicles are liposomes, biocompatible polymers, including natural polymers and synthetic polymers; lipoproteins; polypeptides; polysaccharides; lipopolysaccharides; artificial viral envelopes; metal particles; and bacteria, viruses, such as baculovirus, adenovirus and retrovirus, bacteriophage, cosmid, plasmid, fungal vectors and other recombinant vehicles typically used in the art which have been described in a variety of eukaryotic and prokaryotic hosts. In some embodiments, the nucleic acid delivery vehicle is an expression vector such as a plasmid. The vector may include any element to establish a conventional function of an expression vector (for example, a promoter, ribosome binding element, terminator, enhancer, selection marker), and an origin of replication. The promoter can be a constitutive, inducible or repressible promoter. A number of expression vectors capable of delivering nucleic acids to a cell are known in the art and may be used herein for production of a fusion protein or fusion protein component in the cell. Expressed fusion proteins or fusion protein components can be harvested from the cells and purified according to conventional techniques known in the art and as described herein.

Provided herein are host cells comprising a nucleic acid encoding a fusion protein described herein. Nucleic acids encoding fusion proteins or fusion protein components (e.g., an extracellular portion of an angiogenic factor receptor, a disintegrin or its variant and/or a constant sub-region of an immunoglobulin) can be provided to a target cell by any means known in the art. In some embodiments, the nucleic acid encoding a protein of interest is in an expression vector such as a plasmid. In other embodiments, the nucleic acid encoding a protein of interest is in a viral vector and the vector has been packaged, then the virions can be used to infect cells. Transfection and transformation procedures are known to be appropriately used to introduce a nucleic acid encoding a protein of interest into a target cell. Formulations utilizing polymers, liposomes, or nanospheres can be used for delivery of nucleic acids encoding a protein of interest. Cells which are transformed or transfected with recombinant constructs according to the invention may be any which are convenient to one skilled in the art. Exemplary cell types which may be used include bacteria, yeast, fungi, insect, plant, and mammalian cells. In some embodiments, transformed or transfected cells can be provided to a cell or mammalian host. Suitable cells for delivery to a cell or mammalian host include any mammalian cell type from any origin, tumor, or cell line.

Cells used to produce the fusion proteins or fusion protein components of the invention are grown in media known to those skilled in the art and suitable for culture of the selected host cells. A given medium is generally supplemented as necessary with hormones and/or other growth factors, DHFR, salts, buffers, nucleosides, antibiotics, trace elements, and glucose or an equivalent energy source. Any other necessary supplements may also be included at appropriate concentrations that would be known to those skilled in the art. The culture conditions, such as temperature, pH, and the like, are those previously used with the cell selected for expression, and will be apparent to one skilled in the art.

Proteins may be purified and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable binding partner immobilized on a matrix, centrifugation, Enzyme-Linked Immunosorbent Assay (ELISA), BIACore, Western blot assay, amino acid and nucleic acid sequencing, and biological activity. In some embodiments, the fusion protein is expressed in host cells and purified therefrom using a combination of one or more standard purification techniques, including, but not limited to Protein A affinity chromatography, Protein G affinity chromatography, buffer exchange, size exclusion chromatography, ultrafiltration, and dialysis. Accordingly, the recovered fusion protein is substantially pure. In a further embodiment, the recovered fusion protein is at least any of 90%, 95%, 96%, 97%, 98% or 99% pure.

The fusion proteins or fusion protein components disclosed herein may be characterized or assessed for biological activities including, but not limited to, affinity to a target binding partner, competitive binding, inhibitory activity, inhibition of cell proliferation, inhibition of tumor growth, and inhibition of angiogenesis. In some embodiments, the fusion proteins or fusion protein components disclosed herein can be assessed for biological activity in vitro and in vivo. Many methods for assessing binding affinity are known in the art and can be used to identify the binding affinities of fusion proteins or fusion protein components to a binding partner. Binding affinities can be expressed as dissociation constant (Kd) values or half maximal effective concentration ($EC_{50}$) values.

In any of the embodiments herein, a fusion protein has an EC50 of less than or equal to 1 M, 100 nM, 10 nM, 1 nM, 0.1 nM, 0.01 nM, or 0.001 nM for inhibition of an activity (e.g., inhibition of angiogenic factor activity and/or integrin activity). In any of the embodiments herein, a fusion protein has a Kd for a binding partner (angiogenic factor and/or integrin) of less than about 1.0 mM, 500 µM, 100 µM, 50 µM, 10 µM, 5 µM, 1 µM, 500 nM, 100 nM, 50 nM, 10 nM, 5 nM, 1 nM, 500 pM, 100 pM, 50 pM, 10 pM or 5 pM, including any values in between these numbers.

The invention also provides a pharmaceutical composition comprising a fusion protein comprising an integrin binding peptide selected from a group consisting of disintegrin, anti-integrin αvβx antibody, anti-integrin α5β1 antibody, fibronectin targeting integrin αvβx or α5β1 and their integrin binding fragments, other protein binding peptide targeting an angiogenic factor and a Fc domain, wherein x is 1, 3, 5, 6 or 8. Compositions of the invention comprise a therapeutically effective amount of the fusion protein.

The term "therapeutically effective amount" means an amount of a therapeutically active compound needed to elicit the desired biological or clinical effect. According to embodiments of the invention, "a therapeutically effective amount" is an amount sufficient to effect beneficial or desired results, including clinical results. A therapeutically effective amount can be administered in one or more administrations. In terms of a disease state, a therapeutically effective amount is an amount sufficient to ameliorate, stabilize, or delay development of a disease. According to specific embodiments of the invention, a therapeutically effective amount is an amount of a fusion protein needed to treat or prevent a disorder characterized by abnormal angiogenesis, such as a disease characterized by neovascularization, vascular permeability, edema, inflammation, retinopathies, fibrosis or cancer.

In some embodiments, the pharmaceutical composition comprising a fusion protein comprises a fusion protein formulated in a buffer at a protein concentration from about 0.5 to about 100 mg/mL, preferably about 40 to about 80 mg/mL, such as about 40, 50, 60, 70 or 80 mg/mL, most preferably about 40±about 5 mg/mL. In other preferred embodiments, the fusion protein is formulated in a buffer at a protein concentration of more than about 40 mg/mL.

In particular embodiments, the buffer is a phosphate buffer with a pH of about 6.5 to 8, more preferably about 7 to 7.5, even more preferably about 7.2. The phosphate buffer comprises about 5 to 20 mM sodium phosphate, such as 5, 10, 15 or 20 mM sodium phosphate, more preferably about 10 mM sodium phosphate; about 20 to 60 mM sodium chloride, more preferably about 40 mM sodium chloride; about 1 to 10% weight-per-volume (w/v) sucrose, more preferably about 5% w/v sucrose; and about 0.01 to 0.05% w/v of a surfactant, more preferably about 0.03% w/v polysorbate 20.

In other particular embodiments, the buffer is a histidine buffer with a pH of about 5 to 8, more preferably about 6 to 7, most preferably about 6.8. The histidine buffer comprises about 10 to 50 mM histidine, such as 10, 20, 30, 40 or 50 mM histidine, more preferably about 25 mM histidine; about 10 to 30 mM sodium chloride, such as 10, 20 or 30 mM sodium chloride, more preferably about 20 mM sodium chloride; about 1 to 10% w/v sucrose, such as 1, 2, 4, 6, 8 or 10% w/v sucrose, more preferably about 6% w/v sucrose; and about 0.01 to 0.05% w/v of a surfactant, more preferably about 0.03% w/v polysorbate 20.

The present invention also relates to a use of the composition according to the present invention to treat or prevent an integrin-associated disease in an individual or a subject. An "individual" or "subject" is a mammal. Mammals include, but are not limited to, domesticated animals (e.g., cows, sheep, cats, dogs, and horses), primates (e.g., humans and non-human primates such as monkeys), rabbits and rodents (e.g., mice and rats). In some embodiments, a method of treating or preventing one or more aspects or symptoms of a disease comprises administering an effective amount of a composition comprising the fusion protein to an individual.

The methods described herein can be used for the treatment of a variety of diseases, including but not limited to, inflammatory disease, ocular disease, autoimmune disease, or cancer. In some embodiments, the disease to be treated includes, but is not limited to, rheumatoid arthritis, inflammatory arthritis, osteoarthritis, cancer, fibrosis, retinitis pigmentosa, uveitis (such as anterior uveitis or posterior uveitis and ocular disease characterized by neovascularization or ischemia (such as choroidal neovascularization, diabetic retinopathy, diabetic macular edema, age-related macular degeneration (AMD), retinal vein occlusion, polypoidal choroidal vascularization.

The compositions described herein can be administered to an individual via any route, including, but not limited to, intravenous, intraperitoneal, ocular, intra-arterial, intrapulmonary, oral, inhalation, intravesicular, intramuscular, intra-tracheal, subcutaneous, intrathecal, transdermal, transpleural, intraarterial, topical, inhalational, mucosal, subcutaneous, transdermal, gastrointestinal, intraarticular, intracisternal, intraventricular, intracranial, intraurethral, intrahepatic and intratumoral. In some embodiments, the compositions are administered systemically (for example by intravenous injection). In some embodiments, the compositions are administered locally (for example by intraarterial or intraocular injection).

In some embodiments, the compositions are administered directly to the eye or the eye tissue. In some embodiments, the compositions are administered topically to the eye, for example, in eye drops. In some embodiments, the compositions are administered by injection to the eye (intraocular injection) or to the tissues associated with the eye. The compositions can be administered, for example, by intraocular injection, periocular injection, subretinal injection, intravitreal injection, superchoroidal injection, trans-septal injection, subscleral injection, intrachoroidal injection, intracameral injection, subconjunctival injection, sub-Tenon's injection, retrobulbar injection, peribulbar injection, or posterior juxtascleral delivery. These methods are known in the art. The compositions may be administered, for example, to the vitreous, aqueous humor, sclera, conjunctiva, the area between the sclera and conjunctiva, the retina choroids tissues, macula, or other area in or proximate to the eye of an individual.

The optimal effective amount of the compositions can be determined empirically and will depend on the type and severity of the disease, route of administration, disease progression and health, mass and body area of the individual. Such determinations are within the skill of one in the art. Compositions comprising a fusion protein can also be administered six times a week, five times a week, four times a week, three times a week, twice a week, once a week, once every two weeks, once every three weeks, once a month, once every two months, once every three months, once every six months, once every nine months, or once every year.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

The present invention is further illustrated by the following Examples, which are provided for the purpose of demonstration rather than limitation.

Example 1: Production of Rhodostomin Mutant Proteins

Method of Disintegrin Expression

Overlap extension polymerase chain reaction (PCR) techniques were used to create Rhodostomin (Rho) mutant constructs. The expression kit and the yeast transfer vector, pPICZaA, were purchased from Invitrogen. The gene mutant constructs were created by PCR-amplifying the gene sequence using a sense primer containing a complementary sequence to the gene mutant plus an EcoR1 recognition site and six histidine residues for facilitating purification, and the antisense primer designed to contain a Sac II recognition site and TTA stop codon. The PCR product was purified and then cloned into the EcoR1 and Sac II sites of yeast recombination vector, pPICZaA. The recombinant plasmid was transformed into *E. coli* competent cell DH5a, and colonies were selected by agar plate with low salt Luria Broth (LB, 1% tryptone, 0.5% yeast extract, 0.5% NaCl, and 1.5% agar at pH 7.0) and 25 µg/mL of the antibiotic Zeocin. A single colony was selected to amplify the plasmid for sequencing. After the clones had been confirmed by DNA sequencing, 10 µg of the plasmid was prepared and then linearized by digesting with Sac I enzyme. The linearized construct was transformed into the *Pichia* strain X33 using a kit (*Pichia* EasyComp; Invitrogen), and colonies were selected by agar plate using YPDS (1% yeast extract, 2% peptone, 2% glucose, 2% agar, and 1 M Sorbitol) and 100 µg/mL of Zeocin. PCR analysis was used to analyze *Pichia* integrants to determine whether the gene had integrated into the *Pichia* genome. From a number of clones with multiple copies of gene insertion, clones with the highest protein expression were chosen.

Method of Disintegrin Purification

Rho mutants were produced as follows: 100 µL of cell stock were grown at 30° C. for 48 hours in 200 mL of yeast extract peptone dextrose (YPD) medium (1% yeast extract, 2% peptone, and 2% dextrose) and 100 µg/mL Zeocin. Cells were then transferred into 800 mL of YPD medium. After another 48 hours, the cells were collected by centrifugation and grown in 1 L of minimal methanol medium (1.34% yeast nitrogen base (YNB) with ammonium sulfate without amino acids, $4 \times 10^{-5}$% biotin, and 1% Methanol). Once every 24 hours, 1% methanol was added to induce protein expression for 2 days. The supernatant was collected after centrifugation and dialyzed twice against 5 L of $H_2O$ and once against 5 L of 20 mM Tris-HCl and 200 mM NaCl at pH 8. The final solution was loaded into a nickel-chelating column and eluted with a gradient of 200 mM imidazole. The recombinant Rho proteins produced in *P. pastoris* were further purified by reverse-phase C18 HPLC with a gradient of 15% to 18% acetonitrile. A tricine-SDS-PAGE analysis confirmed that the purification of proteins was greater than 95%.

Example 2: Generation of VEGFR/Rho Mutant Fusion Proteins

The extracellular domain D2 of the Flt-1 receptor (VEGFR1) of SEQ ID NO: 8 and the extracellular domain D3 of the Flt-1 receptor (VEGFR2) of SEQ ID NO: 9, collectively known as VEGF trap, provided the protein component for binding to VEGF ligand. In order to bind to both VEGF ligand and integrins, fusion proteins comprising VEGFR1 D2/VEGFR2 D3 of SEQ ID NO: 10 and Rho mutant of SEQ ID NO: 13 were generated.

A previously generated VEGF trap linked to human immunoglobulin G1 CH2 and CH3 domains (IgG1 Fc) was used to generate DNA constructs encoding the VEGFR1 D2/VEGFR2 D3-Rho mutant hybrid. See Holash, J., et al., PNAS, 2002, 99 (17): 11393-11398 for a description of the VEGF trap which is incorporated herein by reference in its entirety. A fusion protein of SEQ ID NO: 16 was constructed by linking the VEGFR1 D2/VEGFR2 D3 of SEQ ID NO: 10 and Rho mutant of SEQ ID NO: 13 via at least one peptide linker of Gly-Gly-Gly-Gly-Ser ($G_4S$).

Similarly, Fusion Proteins 2 and 3 of SEQ ID NOs: 15 and 17 were also generated by fusing Rho mutants of SEQ ID NO: 12 and SEQ ID NO: 14 respectively with the VEGFR1 D2/VEGFR2 D3 of SEQ ID NO: 10. Fusion Protein 4 of SEQ ID NO: 18 was generated by fusing a commercially available VEGF Trap, aflibercept (Eylea®, Regeneron) and Rho mutant of SEQ ID NO: 13. FIG. 1 provides a schematic showing the structure of a fusion protein according to one embodiment of the invention. SS is a signal peptide sequence of SEQ ID NO: 20 which helps secretion of protein from the CHO cell. VEGF trap is made up of the extracellular Ig-like domains 2 and 3 of human VEGFR1 and VEGFR2. An Fc fragment is the CH2 and CH3 region of human IgG1. A GS is a linker. Rho mutants have been described in U.S. Pat. No. 7,943,728 and PCT Application No. PCT/US 15/46322 and their sequences are incorporated herein by reference.

To generate Fusion Protein 1, which has the amino acid sequence of SEQ ID NO: 16, the DNA sequence encoding Fusion Protein 1 was codon-optimized for expression in CHO cells. The synthesized codon-optimized DNA, with a nucleic acid sequence of SEQ ID NO: 19, together with the signal peptide having a nucleic acid sequence of SEQ ID NO: 21 was cloned into an expression vector. CHO K1 host cells were seeded at 2×105 cells/mL in CD CHO (Gibco 12490-003) containing 4 mM Glutamine (J.T Baker 2078-06) and 1% HT Supplement (Gibco 11067-030) 72 hours before transfection. The host cells were incubated in an Infors shaker (36.5° C., 75% humidity, 6% $CO_2$, 110 RPM) and counted for cell density before use. A suitable amount of expression plasmid DNA was added into the host cells (1 L or 5 L working volume), and polymer-based transfection reagent was added. The transfected cultures were incubated in an Infors shaker (36.5° C., 75% humidity, 6% $CO_2$, 110 RPM) for 4 hours and a proprietary feed solution was added. The transfected cultures were then incubated in an Infors shaker (32° C., 75% humidity, 6% $CO_2$, 110 RPM). The transfected cultures were harvested on day 10 after transfection. The supernatants were purified for generation of research materials. The purification process included clarification, Protein A affinity chromatography, concentration by Amicon Ultracel, size exclusion chromatography, dialysis by Slide-A-Lyzer, and final concentration by Amicon Ultracel in the formulation buffer.

Figure 2:
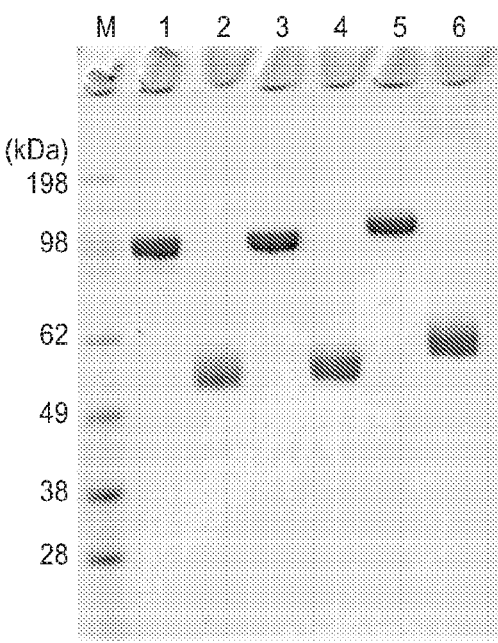
FIG. 2 is a schematic illustrating the purified Fusion Protein 1 analyzed by SDS-PAGE.

Fusion proteins having simultaneous anti-VEGF and anti-integrin activities were constructed, expressed, purified and characterized. FIG. 2 provides a schematic characterizing the purified Fusion Protein 1 by SDS-PAGE. The molecular marker was loaded in Lane M. Non-reduced and reduced forms of engineered VEGF-trap (Positive Control 1; SEQ ID NO: 23) consisting of portions of human VEGFR1 and VEGFR2 fused to the Fc portion of human IgG1 were loaded in Lanes 1 and 2, respectively. Non-reduced and reduced forms of commercially available VEGF-trap, aflibercept (Eylea®, Regeneron) (Positive Control 2) were loaded in Lanes 3 and 4, respectively. Non-reduced and reduced forms of Fusion Protein 1 were loaded in Lanes 5 and 6. Each protein sample was loaded in the volume of 3 μg in each lane. As shown in FIG. 2, the results indicate that both the positive control and Fusion Protein 1 exhibited high integrity and purity under reducing and non-reducing conditions. The final concentration of Fusion Protein 1 was approximately 40 mg/mL in the designated formulation buffer (based on the absorption at 280 nm).

Production of protein homodimers by cell transfection with their respective constructs was confirmed by SDS-PAGE and bioactivity analysis.

Example 3: Binding Affinity of Fusion Protein to Human $VEGF_{165}$

A direct binding enzyme-linked immunosorbent assay (ELISA) was used to measure the binding affinity of fusion proteins of the invention to human $VEGF_{165}$, a splice variant of VEGF-A.

VEGF Trap is a soluble VEGF receptor that was engineered for therapeutic use and is currently approved by FDA to treat AMD. The VEGF Trap contains the second Ig-like domain 2 (D2) of VEGFR1 fused to the third Ig-like domain 3 (D3) of VEGFR2 fused to the Fc region of human IgG1 (Holash, J., et al, Proc Natl Acad Sci USA. 2002 Aug. 20; 99(17):11393-8). VEGF Trap targets VEGF-A, VEGF-B, and PlGF. The commercially available VEGF Trap, aflibercept (Eylea®, Regeneron), was included as Positive Control 2.

100 μL of a coating solution (1 μg/mL $VEGF_{165}$ in 1× phosphate buffered saline (PBS), pH 7.2) were added to each well of a 96-well ELISA plate, and the plate was incubated overnight at 4° C. The wells were washed twice with 400 μL of 1×PBS buffer, and excess liquid was carefully removed with a paper towel.

400 μL of a blocking solution (5 g non-fat skim milk in 100 mL 1×PBS) were added to each well, and the plate was incubated at room temperature for 1 hour. The wells were washed twice with 1×PBS buffer.

Fusion protein and control samples were serially diluted three-fold in blocking solution, with a highest protein concentration of 10 nM. 100 μL of the serially diluted samples were added to each well. The plate was covered and incubated on a plate shaker (~100 rpm) for 1 hour at room temperature. The wells were washed three times with wash buffer (1×PBS, 0.05% Tween-20).

100 μL of 1:2500 diluted horseradish peroxidase-conjugated goat anti-human IgG Fc specific antibodies in blocking solution were added to each well. The plates were sealed and incubated on a plate shaker for 1 hour at room temperature. The plates were washed three times with wash buffer.

100 μL of 3,5,3',5'-Tetramethylbenzidine (TMB) were added to each well, and the plates were incubated for 3 to 5 minutes to allow for the reaction to take place. To stop the reaction, 100 μL of stop solution (1N HCl) were added to each well.

The optical density (OD) of each well was determined using an ELISA plate reader at an absorbance wavelength of 450 nm. The absorbance was plotted against the protein concentration of the fusion protein or the control, and the concentration at which the signal was half the maximal effective concentration ($EC_{50}$) was determined.

The binding affinity, expressed as the $EC_{50}$ value, was between 0.10 and 0.21 nM for the tested fusion proteins of the invention. The ELISA results are shown in Table 2

TABLE 2

| Test Material | $EC_{50}$ (nM) |
| --- | --- |
| Positive Control 2 (aflibercept) | 0.088-0.195 |
| Fusion Protein 1 (SEQ ID NO: 16) | 0.106-0.207 |

Figure 3:
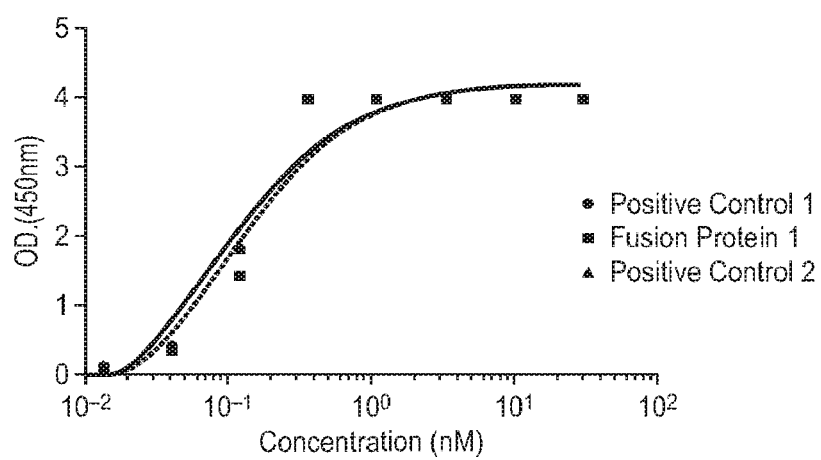
FIG. 3 is a schematic illustrating a VEGF-ligand binding assay.

Results from Example 3 showed that fusion proteins according to embodiments of the invention, bind $VEGF_{165}$ with high affinity. This is also illustrated in FIG. 3.

Example 4—Competitive Binding of Fusion Protein to Integrin αvβ3

The competitive binding was used to measure the binding affinity of Fusion Protein 1 of the invention to integrin αvβ3. Wild type Rho (SEQ ID NO: 1) and Rho variant KG (SEQ ID NO: 13) were synthesized in accordance with example 1 and included as Positive Control 3 and Positive Control 4 respectively in the competitive binding assay.

1 μg/mL victronectin dissolved in coating solution were added to each well of a 96-well ELISA plate, and the plate was incubated overnight at 4° C. The wells were washed twice with PBS buffer, and excess liquid was carefully removed with a paper towel.

Blocking solution (5 g non-fat skim milk in 100 mL 1×PBS) were added to each well, and the plate was incubated at room temperature for 1 hour. The wells were washed twice with 1×PBS buffer.

Various concentrations of Positive Control 3, Positive Control 4, and Fusion Protein 1 were mixed with certain concentration of soluble integrin αvβ3. One hundred microliters (100 L) of the serially diluted samples were added to each well. The plate was covered and incubated on a plate shaker (~100 rpm) for 1 hour at room temperature. The wells were washed three times with wash buffer (1×PBS, 0.05% Tween-20).

Diluted primary anti-integrin αv antibody was added and incubated, then washed. Horseradish peroxidase-conjugated goat anti-human IgG Fc specific antibodies in blocking solution were added to each well. The plates were sealed and incubated on a plate shaker for 1 hour at room temperature. The plates were washed three times with wash buffer.

100 μL of 3,5,3',5'-Tetramethylbenzidine (TMB) were added to each well, and the plates were incubated for 3 to 5 minutes to allow for the reaction to take place. To stop the reaction, 100 μL of stop solution (1N HCl) were added to each well.

The optical density (OD) of each well was determined using an ELISA plate reader at an absorbance wavelength of 450 nm. The absorbance was plotted against the protein concentration of the fusion protein or the control, and the concentration at which the signal was half the maximal inhibition concentration ($IC_{50}$) was determined.

Figure 4:
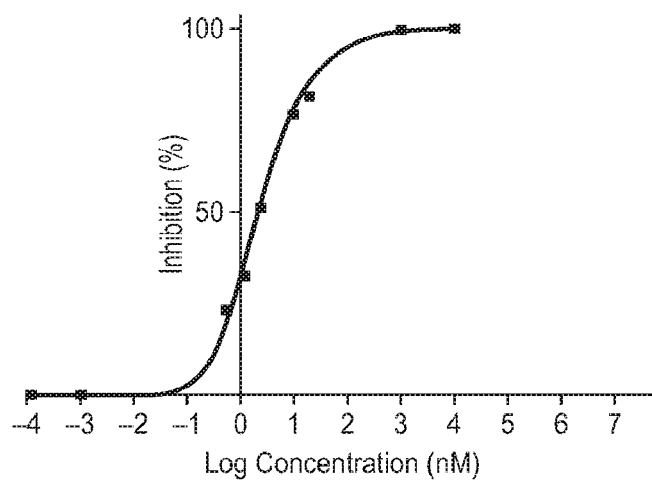
FIG. 4 is a schematic illustrating a αvβ3 competitive binding assay.

The competitive binding, expressed as the $IC_{50}$ value, was between 2.2 and 16 nM for the tested fusion protein of the invention. The results are shown in Table 3 and also illustrated in FIG. 4.

TABLE 3

| Test Material | $IC_{50}$ (nM) |
| --- | --- |
| Positive Control 3 (wild type Rho, SEQ ID NO: 1) | 2.6-3.2 |
| Positive Control 4 (Rho variant KG, SEQ ID NO: 13) | 2.2-2.9 |
| Fusion Protein 1 (SEQ ID NO: 16) | 2.2-16.0 |

Example 5—Inhibition of HUVEC Proliferation by Fusion Protein

A human umbilical vein endothelial cell (HUVEC) proliferation assay was carried out to test the functionality of the fusion proteins of the invention. A commercially available VEGF Trap, aflibercept (Eylea®, Regeneron), was included as Positive Control 2.

100 μL of a coating solution (1% gelatin in double distilled water) were added to each well of a 96-well ELISA plate, and the plate was incubated for 2 hours or overnight at 37° C. The wells were washed twice with 1×PBS buffer.

3500 counts of human umbilical vein endothelial cells in endothelial cell growth medium were added to each well, and the plate was incubated overnight at 37° C.

Fusion protein samples were diluted in assay buffer (Medium-199 1× Earle's Salts, 10% fetal bovine serum, 10 mM HEPES, 1× antibiotic/antimycotic), with a highest protein concentration of 300 nM. The fusion protein samples were mixed with $VEGF_{165}$ (8 ng/mL), and the mixtures were incubated overnight at room temperature. The wells were then washed with 200 μL of 1×PBS.

100 μL of the $VEGF_{165}$/sample mixture were added to each well, and the plates were incubated for 72 hours at 37° C. with 5% $CO_2$. Following incubation, 10 μL MTS detection reagent (3-(4,5-dimethylthiazol-2-yl)-5-(3-carboxymethoxyphenyl)-2-(4-sulfophenyl)-2H-tetrazolium)+ phenazine methosulfate in distilled PBS) were added to each well, and the plates were incubated at 37° C. for 2.5 hours.

The OD of each well was determined using an ELISA plate reader at an absorbance wavelength of 490 nm. The absorbance was plotted against the protein concentration of the fusion protein or the control, and the concentration at which the cell proliferation was inhibited by 50% ($IC_{50}$) was determined.

Figure 5:
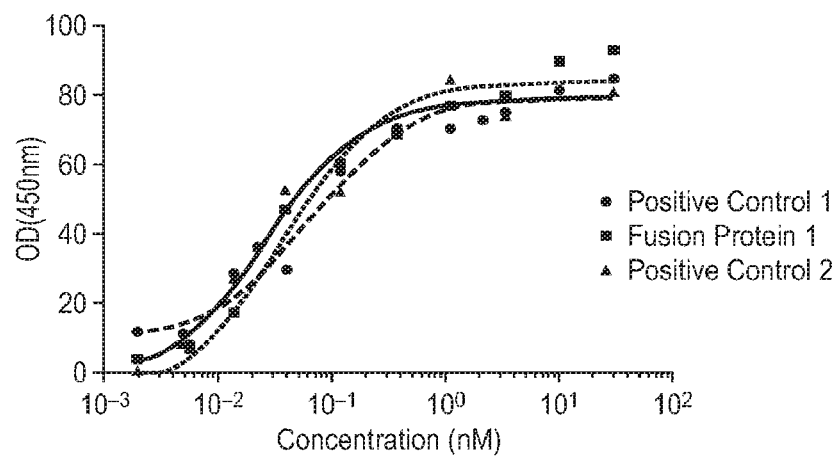
FIG. 5 is a schematic illustrating VEGF-induced HUVEC proliferation.

The inhibition of cell proliferation ($IC_{50}$) was determined to be between 0.039 and 0.103 nM for the tested fusion protein of the invention. The results of the proliferation assay are shown in Table 4 and they are also illustrated in FIG. 5. Both Positive Control 2 and Fusion Protein 1 exhibited similar activity on the inhibition of VEGF dependent HUVEC proliferation.

TABLE 4

| Test Material | $IC_{50}$ (nM) |
| --- | --- |
| Positive Control 2 (aflibercept) | 0.026-0.136 |
| Fusion Protein 1 (SEQ ID NO: 16) | 0.039-0.103 |

Example 6—Inhibition of αvβ3 and α5β1 Cell Adhesion by Fusion Protein

The adhesion of αvβ3-overexpressing CHO cells to fibrinogen and α5β1-expressing K562 cells to fibronectin were evaluated in the presence of fusion proteins.

96-well Immulon-2 microtiter plates (Costar, Corning, NY) were coated with 100 μL of phosphate-buffered saline (PBS: 10 mM phosphate buffer, 0.15 M NaCl, pH 7.4) containing substrates at a concentration of 50-500 nM, and incubated overnight at 4° C. The substrates and their coating concentrations were fibrinogen (Fg) at 200 μg/mL and fibronectin (Fn) at 25 μg/mL. Non-specific protein binding sites were blocked by incubating each well with 200 μL of heat-denatured 1% bovine serum albumin (BSA) (Calbiochem) at room temperature for 1.5 hours. The heat-denatured BSA was discarded and each well was washed twice with 200 μL of PBS.

CHO cells that expressed the integrin αvβ3 (CHO-αvβ3) from the same source of Patent Application No. PCT/US2015/46322 were maintained in DMEM. Human erythroleukemia K562 was maintained as written in Patent Application No. PCT/US2015/46322 from ATCC and cultured in Roswell Park Memorial Institute (RPMI)-1640 medium containing 5% FCS. Harvested K562 was washed in PBS buffer containing 1 mM EDTA and resuspended in Tyrode's buffer (150 mM NaCl, 5 mM KCl, and 10 mM HEPES, pH 7.35) containing 1 mM $MgSO_4$, 2 mM $CaCl_2$, and 500 μM $MnCl_2$. Cells (CHO and K562) were diluted to $3\times10^5$ cells/mL, and 100 μL of the cells were used for the assay. Rho and it mutants were added to the cultured cells and incubated at 37° C., 5% $CO_2$ for 15 minutes. Rho and its variants were used as inhibitors at the concentrations of 0.001-500 μM. The treated cells were then added into the coated plate and incubated at 37° C., 5% $CO_2$ for 1 hour. The incubation solution was then discarded and non-adhered cells were removed by washing twice with 200 μL PBS. Bound cells were quantified by crystal violet staining. Briefly, the well was fixed with 100 μL of 10% formalin for 10 minutes and dried. Fifty microliters (50 μL) of 0.05% crystal violet were then added into the well at room temperature for 20 minutes. Each well was washed with 200 μL of distilled water four times and dried. Colorization was carried out by adding 150 μL of colorizing solution (50% alcohol and 0.1% acetic acid). The resulting absorbance was read at 600 nm and the readings were correlated with the number of adhering cells.

Inhibition calculation of cell adhesion was conducted according to the following equation.

$$\% \text{ Inhibition} = 100 - \frac{OD_{600}(TA) - OD_{600}(NC)}{OD_{600}(PC) - OD_{600}(NC)} \times 100$$

In the above equation, TA refers to a "test article"; NC refers to "negative control", and PC refers to "positive control".

Figure 6:
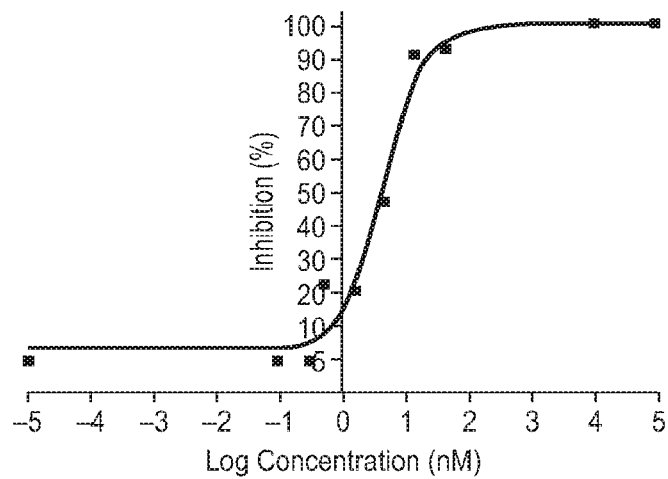
FIG. 6 is a schematic illustrating the inhibition of CHO-αvβ3 cell adhesion.
Figure 7A:
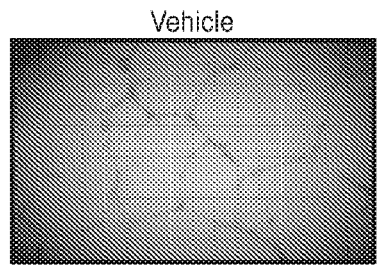
FIGS. 7A-G is a schematic illustrating tube formation inhibitory effect by Fusion Proteins.
Figure 7E:
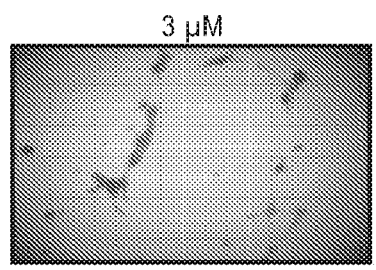
Figure 7B:
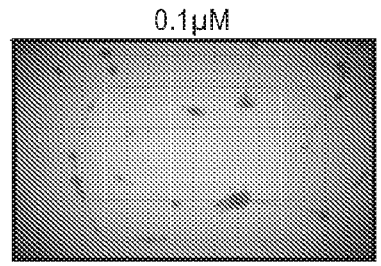
Figure 7F:
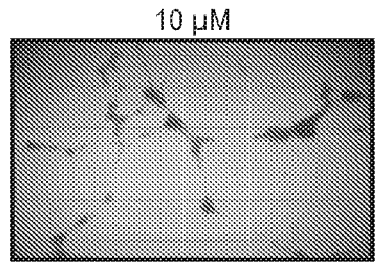
Figure 7C:
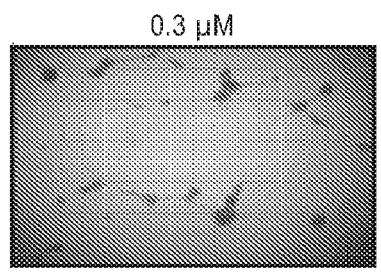
Figure 7G:
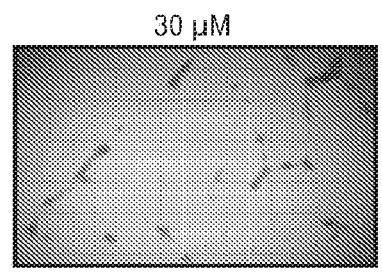
Figure 7D:
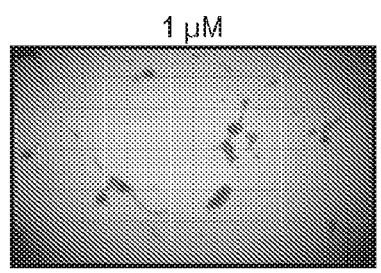
Figure 8A:
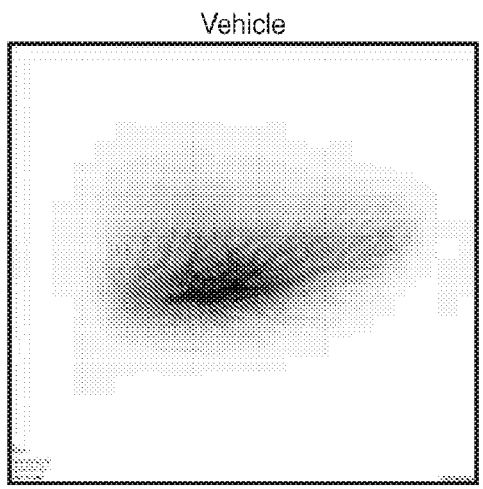
FIGS. 8A-D provide one embodiment showing the dose-response inhibition of VEGF-induced leakage in Dutch Belted Rabbits by Fusion Proteins.
Figure 8B:
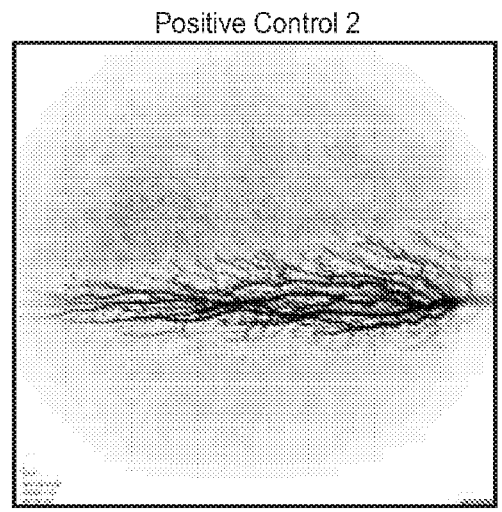
Figure 8C:
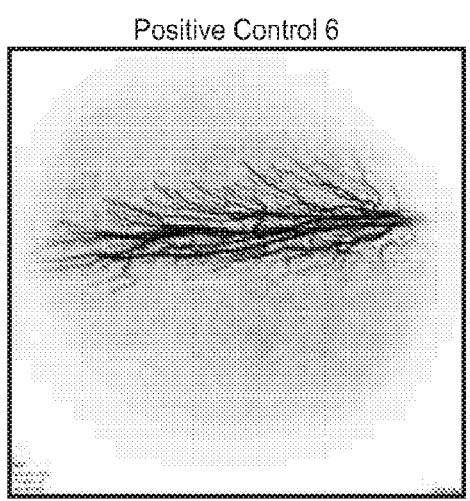
Figure 8D:
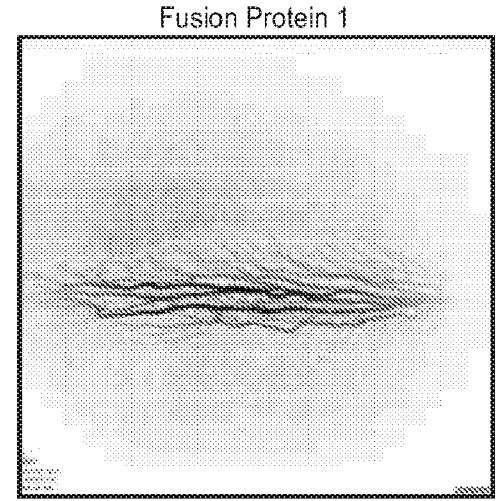

The $IC_{50}$ was defined as the concentration (nM) of a disintegrin variant required for 50% inhibition of the cell adhesion mediated by a particular integrin. Therefore, lower $IC_{50}$ indicates greater specificity or potency of the disintegrin variant in inhibiting the cell adhesion activity of the respective integrin, thus higher binding activity (or selectivity) of the disintegrin variant to the respective integrin. The $IC_{50}$ results are summarized in Table 5. FIG. 6 provides a schematic showing the inhibition of CHO-αvβ3 cell adhesion by Fusion Protein 1.

TABLE 5

| Test Material | αvβ3, $IC_{50}$ (nM) | α5β1, $IC_{50}$ (nM) |
|---|---|---|
| Positive Control 3 (SEQ ID NO: 1) | 24.7 | 252.5 |
| Positive Control 4 (SEQ ID NO: 13) | 19.6 | 17.5 |
| Fusion Protein 1 (SEQ ID NO: 16) | 4.76 | 3.4 |

Example 7: Inhibition of HUVEC Tube Formation by Fusion Protein

HUVECs ($1.5\times10^4$ cells/well) were placed in a 96-well matrigel-coated plate. Six doses of Fusion Protein 1 (0.1 μM, 0.3 μM, 1 μM, 3 μM, 10 μM, and 30 μM) and vehicle were added to each well in growth media under an atmosphere of 5% $CO_2$ at 37° C. After an 18-hour incubation period, morphology of the endothelial cell tubes, which resemble a capillary-like network, were evaluated by photomicroscopy. Disruption (anti-angiogenesis) of total tube length was measured from each photograph and determined relative to the vehicle control group. Minimum inhibitory concentration (MIC≥30%) of tube formation was then determined and used to assess the degree of anti-angiogenesis. Suramin was used as an anti-angiogenic positive control (Positive Control 5) for all studies.

The inhibition of tube formation ($IC_{50}$) was determined to be less than 0.1 μM for the tested Fusion Protein 1 which showed a higher potency than Positive Control 4. The results of the tube formation assay are shown in Table 6. FIGS. 7A-G provide a schematic showing the inhibitory effect of Fusion Protein 1 on tube formation when Fusion Protein 1 was added at a dose of 0.1 μM, 0.3 μM, 1 μM, 3 μM, 10 μM, and 30 μM, respectively.

TABLE 6

| Test Material | $IC_{50}$ (μM) |
|---|---|
| Positive Control 5 (Suramin ®) | 15.8 |
| Positive Control 4 (SEQ ID NO: 13) | 5.9 |
| Fusion Protein 1 (SEQ ID NO: 16) | <0.1 |

Example 8—Inhibition of VEGF-Induced Leakage in Dutch Belted Rabbits by Fusion Proteins Fusion proteins of the invention were tested in an in vivo model of vascular permeability to determine their efficacy in preventing vascular leakage. In this model, VEGF was intravitreally injected to the vitreous of rabbit eyes to induce uncontrolled retinal leakage. Aflibercept (Eylea®, Regeneron), a recombinant fusion protein consisting of portions of human VEGFR1 and VEGFR2 fused to the Fc portion of human IgG1, and bevacizumab (Avastin®, Roche), a recombinant humanized monoclonal antibody that blocks angiogenesis by inhibiting VEGF-A were included as Positive Controls 2 and 6, respectively.

In one embodiment, a pharmaceutical composition contained 20,000 μg/mL of Fusion Protein 1 in a formulation buffer comprising 25 mM histidine buffer, 20 mM NaCl, 6% (w/v) sucrose, 0.03% (w/v) polysorbate, pH 6.0.

Dutch Belted rabbits were anesthetized using isoflurane (3-5%), and their eyes were treated with ophthalmic Betadine solution. The rabbits' eyes were then washed with sterile saline, and lidocaine hydrochloride (2% injectable) or proparacaine (0.5%) was applied to the ocular surface.

On Day 1, Dutch Belted rabbits were intravitreally injected with fusion proteins of the invention, vehicle (negative) control, or reference (positive) controls at predetermined doses using a BD 300 μL insulin syringe (31 ga×5⁄16 inch). The needle was inserted through the dorsotemporal quadrant of the eye, approximately 3-4 mm posterior to the limbus and 3-4 mm lateral to the dorsal rectus muscles, and 50 μL of solution was delivered. Vascular leakage was induced by injecting exogenous $VEGF_{165}$ into the same eyes on Day 3.

Fluorescein angiography (FA) was conducted on all dosage groups 3 days after VEGF injection to assess leakiness and tortuosity using a scale from 0 (normal) to 4 (severe).

Signs of ocular irritation were scored using the Draize scoring system prior to fusion protein dosing, VEGF induction, and assessments. According to the Draize analysis, all of the rabbit eyes were normal prior to the initiation of dosing. Transient signs of minimal ocular inflammation were observed in all treatment groups after intravitreal dose administration, and were attributed to the intravitreal procedure. There were no drug-related findings evident during the course of the study.

FAs associated with the vehicle control group had the highest mean score (2.58) associated with retinal vasculature leakiness and tortuosity. The two reference positive control groups 2 and 6 had mean scores of 0 and 0.25, indicating a significant reduction in retinal vasculature leakiness and tortuosity. The tested fusion proteins of the invention had a mean score of 0.167, showing effectiveness in reducing VEGF-induced retinal leakiness and tortuosity comparable to the positive controls. The results of the in vivo assay are shown in Table 7. FIGS. 8A-D provide the representative FAs showing the inhibition of VEGF-induced leakage in Dutch Belted Rabbits by the Fusion Protein 1 and positive controls.

TABLE 7

| Test Material | Dose (µg) | No. of Scores | Day 6 Mean Leakage Score |
|---|---|---|---|
| Vehicle | 0 | 12 | 2.583 |
| Positive Control 6 (bevacizumab) | 1250 | 12 | 0.250 |
| Positive Control 2 (aflibercept) | 625 | 12 | 0 |
| Fusion Protein 1 (SEQ ID NO: 16) | 1000 | 12 | 0.417 |

Example 9—Dose-Response Inhibition of VEGF-Induced Leakage in Dutch Belted Rabbits by Fusion Protein Fusion proteins of the invention were tested in an in vivo model of retinal vascular permeability at varying doses to determine their dose-response effectiveness in preventing vascular leakage. In this model, human $VEGF_{165}$ was intravitreally injected to the vitreous of rabbit eyes to induce retinal leakage.

On Day 1, Dutch Belted rabbits were intravitreally injected with Fusion Protein 1 according to an embodiment of the invention at various doses, vehicle (negative) control, or reference (positive) controls. Vascular leakage was induced by injecting exogenous $VEGF_{165}$ into the same eyes on Day 3.

FAs were conducted on all dosage groups 3 days after the VEGF-induction (Day 6) to assess leakiness and tortuosity using a scale from 0 (normal) to 4 (severe).

Signs of ocular irritation were scored using the Draize scoring system prior to fusion protein dosing, VEGF induction, and assessments. According to the Draize analysis, all of the rabbit eyes were normal prior to the initiation of dosing. Transient signs of minimal ocular inflammation were observed in all treatment groups after intravitreal dose administration, and were attributed to the intravitreal procedure. There were no drug-related findings evident during the course of the study.

For the first exogenous VEGF injection, FAs associated with vehicle control group had the highest mean score (3.4) associated with retinal vasculature leakiness and tortuosity. The two reference positive control groups had mean scores of 0, indicating a significant reduction in retinal vasculature leakiness and tortuosity. The tested fusion protein of the invention (Fusion Protein 1) had scores of 0.08, 0.42, and 0.17 at doses of 100, 500 and 1000 µg, respectively, showing effectiveness in reducing VEGF-induced retinal leakiness and tortuosity comparable to the positive controls.

The results of the dose-response in vitro assay are shown in Table 8.

TABLE 8

| Test Material | Dose (µg) | No. of Scores | Day 6 Mean Leakage Score |
|---|---|---|---|
| Vehicle | 0 | 10 | 3.400 |
| Positive Control 6 (bevacizumab) | 1250 | 12 | 0.17 |
| Positive Control 2 (aflibercept) | 625 | 12 | 0 |
| Fusion Protein 1 (SEQ ID NO: 16) | 1000 | 12 | 0.33 |
| Fusion Protein 1 (SEQ ID NO: 16) | 500 | 10 | 0.40 |
| Fusion Protein 1 (SEQ ID NO: 16) | 100 | 10 | 0.60 |

Example 10—Reduction of Lesion Size in Laser-Induced Choroidal Neovascularization (CNV) in Rats by Fusion Proteins The eyes of Brown Norway rats were dilated with a 1% Cyclogyl solution and protected from light. Following the dilation, the rats were anesthetized using a ketamine and xylazine mixture. Three lesion burns were introduced to the retina of each eye using a laser at 532 nm on Day 1.

On Day 3, the animals were anesthetized with a ketamine and xylazine mixture, their eyes were dilated, and 5 µL of Fusion Protein 1, vehicle (negative control), or Positive Control 2 (reference) at predetermined doses were intravitreally injected into both eyes of an animal using a Hamilton syringe with 33 gauge needle.

Figure 9A:
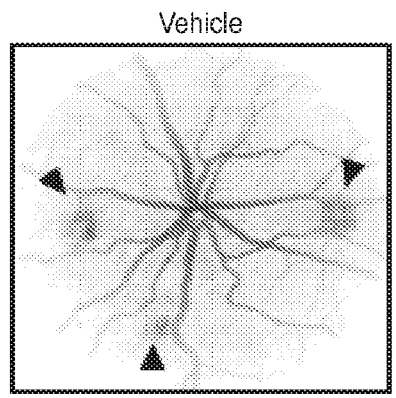
FIGS. 9A-C provide one embodiment showing the reduction of lesion size in laser-induced choroidal neovascularization (CNV) in rats by Fusion Proteins. An arrow (▼) denotes location of laser lesion.
Figure 9B:
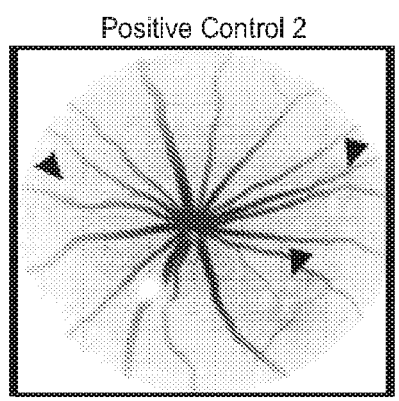
Figure 9C:
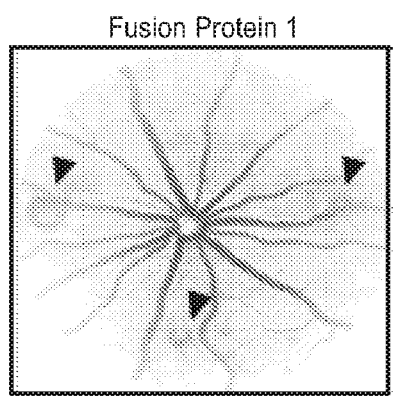

To confirm successful lesion formation, fundus images were taken using a Micron III small animal funduscope (Phoenix Research) prior to lesion introduction, after the lesion burns, and on Day 22. The animals received an IP injection of 10% fluorescein sodium at 1 µL/g of body weight on Day 22 to assess neovascularization of the lesion burns. From fluorescein angiograms, lesion size were determined and compared across dosage groups as shown in FIGS. 9A-C, wherein FIG. 9A shows a schematic of vehicle, FIG. 9B shows a schematic of Positive Control 2, and FIG. 9C shows a schematic of Fusion Protein 1. The arrows (▼) in FIGS. 9A-C indicated laser lesion spots.

Example 11—Reduction of Lesion Size in Laser-Induced CNV in Monkeys by Fusion Proteins The fusion proteins are tested in a laser-induced CNV model established in monkeys. Six to nine burns are introduced around the macula of each eye using 532 nm diode laser photocoagulation, and 0.5-4 mg of fusion proteins of the invention are intravitreally injected on the same day.

The animals are sedated with intravenous 2.5% soluble pentobarbitone (1 mL/kg) 20 days later. The eyelids are fixed to keep the eyes open, and color photographs are taken using a fundus camera.

Fluorescein dye (20% fluorescein sodium; 0.05 mL/kg) is injected into a vein of a lower extremity. Photographs are taken at several time points after injection of the dye, including the arterial phase, early arteriovenous phase, and several late arteriovenous phases, to monitor leakage of fluorescein associated with CNV lesions.

Example 12—Inhibition of Orthotopic Human Glioblastoma Tumor Growth in Xenograft Mice by Fusion Proteins The human glioblastoma cell line U87-MG ($2.5 \times 10^5$ cells/2 μL, Luciferase cells) is implanted into BALB/c nude mice to establish an orthotopic xenograft model.

In order to assess the inhibitory effects of the fusion proteins of the invention on the tumor growth, tumor cells are implanted into nude mice, and various concentrations of fusion proteins according to embodiments of the invention, ranging from 3 to 30 mg/kg, are administered to the mice intravenously twice weekly. The tumor growth, and survival rate of animals are measured weekly for up to 8 weeks.

Example 13—Inhibition of Lung Fibrosis in Bleomycin-Induced Fibrosis Mice by the Fusion Proteins Male C57BL/6 mice weighing 20±2 g are used to induce lung fibrosis and the effect of the fusion proteins on inhibiting fibrosis. Animals are anesthetized with isoflurane and then a single dose of bleomycin at 1.5 IU/kg (dissolved in 25 μl of saline) is administered intratracheally on Day 1. This dose of bleomycin is known to reproducibly generate pulmonary fibrosis and may induce a mortality of 10-20%.

Nintedanib is administered each day by oral gavage at 10-50 mg/kg per day as a positive control. The administration volume is 10 mL/kg body weight. As a negative control, the fusion protein vehicle is administered to the animals by IV injection. A no treatment control is used to monitor the lung pathology changes after bleomycin administration. Various doses of Fusion Protein 1 and vehicle are administered intravenously once a day, starting from Day 1 to Day 21. Clinical observations including body weight are monitored daily. Animals are sacrificed on Day 22. Bronchoalveolar lavage fluid is collected to investigate cell count and TGF-β1.

In order to assess the inhibitory effects of the fusion proteins of the invention on fibrosis formation, lung tissues are removed and homogenized in buffer to measure the change of hydroxyproline compared to a standard curve. Other histopathology experiments are performed to gather expression of fibrosis and inflammatory specific biomarkers.

While the invention has been described in detail, and with reference to specific embodiments thereof, it will be apparent to one of ordinary skill in the art that various changes and modifications can be made therein without departing from the spirit and scope of the invention.

---

What is claimed is:

1. A fusion protein comprising, from N-terminus to C-terminus in the following order:

an extracellular domain of a Vascular Endothelial Growth Factor (VEGF) receptor comprising an Ig-like domain D2 of a VEGFR1 having the amino acid sequence of SEQ ID NO: 8 and an Ig-like domain D3 of VEGFR2 having the amino acid sequence of SEQ ID NO: 9;

a Fc domain;

an integrin binding peptide comprising disintegrin having a binding selectivity for integrin αvβx and α5β1, wherein the integrin binding peptide has a mutated amino acid sequence of SEQ ID NO:1 comprising a first mutation, wherein the amino acid sequence at positions 46 to 53 of SEQ ID NO: 1 is substituted with the amino acid sequence of SEQ ID NO: 26 or SEQ ID NO: 28, and at least one mutation selected from the group consisting of (a) a second mutation, wherein the amino acid sequence at positions 39 to 45 of SEQ ID NO: 1 is substituted with the amino acid sequence of SEQ ID NO: 36; and (b) a third mutation, wherein the amino acid sequence at positions 65 to 68 of SEQ ID NO: 1 is substituted with the amino acid sequence of SEQ ID NO: 42;

wherein x is 3, 5, or 6.

2. The fusion protein according to claim 1, further comprising a GS or $G_9$ linker between the Fc domain and the integrin binding peptide.

3. The fusion protein according to claim 1, further comprising a signal peptide sequence upstream of the extracellular domain of a VEGF receptor.

4. A dimer of the fusion protein according to claim 1.

5. The fusion protein according to claim 1, wherein the integrin binding peptide has the mutated amino acid sequence of SEQ ID NO:1 comprising the first mutation and the second mutation.

6. The fusion protein according to claim 1, wherein the integrin binding peptide has the mutated amino acid sequence of SEQ ID NO:1 comprising the first mutation, the second mutation and the third mutation.

7. A composition comprising the fusion protein according to claim 1 and a pharmaceutically acceptable adjuvant, carrier or excipient.

* * * * *

SEQUENCE LISTING

```
<160> NUMBER OF SEQ ID NOS: 70

<210> SEQ ID NO 1
<211> LENGTH: 68
<212> TYPE: PRT
<213> ORGANISM: Unknown
<220> FEATURE:
<223> OTHER INFORMATION: Rhodostomin

<400> SEQUENCE: 1

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Ser Arg Ala Gly Lys Ile Cys Arg Ile Pro
        35                  40                  45

Arg Gly Asp Met Pro Asp Asp Arg Cys Thr Gly Gln Ser Ala Asp Cys
    50                  55                  60

Pro Arg Tyr His
65

<210> SEQ ID NO 2
<211> LENGTH: 68
<212> TYPE: PRT
<213> ORGANISM: Artificial Sequence
<220> FEATURE:
<221> NAME/KEY: VARIANT
<222> LOCATION: 39, 40, 41, 42, 43, 46, 47, 48, 50, 52, 53, 65, 66, 67,
      68
<223> OTHER INFORMATION: Xaa = Any Amino Acid
<220> FEATURE:
<223> OTHER INFORMATION: Rhodostomin mutant

<400> SEQUENCE: 2

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
```

```
            20                  25                  30
Cys Glu Gln Cys Lys Phe Xaa Xaa Xaa Xaa Ile Cys Xaa Xaa Xaa
            35                  40                  45

Arg Xaa Asp Xaa Xaa Asp Asp Arg Cys Thr Gly Gln Ser Ala Asp Cys
            50                  55                  60

Xaa Xaa Xaa Xaa
 65
```

<210> SEQ ID NO 3
<211> LENGTH: 70
<212> TYPE: PRT
<213> ORGANISM: Unknown
<220> FEATURE:
<223> OTHER INFORMATION: Rhodostomin mutant

<400> SEQUENCE: 3

```
Gly Glu Glu Cys Asp Cys Gly Ser Pro Ser Asn Pro Cys Cys Asp Ala
 1               5                  10                  15

Ala Thr Cys Lys Leu Arg Pro Gly Ala Gln Cys Ala Asp Gly Leu Cys
            20                  25                  30

Cys Asp Gln Cys Arg Phe Lys Lys Lys Arg Thr Ile Cys Arg Ile Ala
            35                  40                  45

Arg Gly Asp Phe Pro Asp Asp Arg Cys Thr Gly Gln Ser Ala Asp Cys
            50                  55                  60

Pro Arg Trp Asn Gly Leu
 65                  70
```

<210> SEQ ID NO 4
<211> LENGTH: 49
<212> TYPE: PRT
<213> ORGANISM: Unknown
<220> FEATURE:
<223> OTHER INFORMATION: Echistatin

<400> SEQUENCE: 4

```
Gln Cys Glu Ser Gly Pro Cys Cys Arg Asn Cys Lys Phe Leu Lys Glu
 1               5                  10                  15

Gly Thr Ile Cys Lys Arg Ala Arg Gly Asp Asp Met Asp Asp Tyr Cys
            20                  25                  30

Asn Gly Lys Thr Cys Asp Cys Pro Arg Asn Pro His Lys Gly Pro Ala
            35                  40                  45

Thr
```

<210> SEQ ID NO 5
<211> LENGTH: 73
<212> TYPE: PRT
<213> ORGANISM: Unknown
<220> FEATURE:
<223> OTHER INFORMATION: Trimucrin

<400> SEQUENCE: 5

```
Glu Ala Gly Glu Glu Cys Asp Cys Gly Ser Pro Glu Asn Pro Cys Cys
 1               5                  10                  15

Asp Ala Ala Thr Cys Lys Leu Arg Pro Gly Ala Gln Cys Ala Glu Gly
            20                  25                  30

Leu Cys Cys Asp Gln Cys Arg Phe Lys Lys Lys Arg Thr Ile Cys Arg
            35                  40                  45

Arg Ala Arg Gly Asp Asn Pro Asp Asp Arg Cys Thr Gly Gln Ser Ala
            50                  55                  60
```

```
Asp Cys Pro Arg Asn Gly Leu Tyr Gly
 65                  70
```

<210> SEQ ID NO 6
<211> LENGTH: 73
<212> TYPE: PRT
<213> ORGANISM: Unknown
<220> FEATURE:
<223> OTHER INFORMATION: Elegantin

<400> SEQUENCE: 6

```
Glu Ala Gly Glu Glu Cys Asp Cys Gly Ser Pro Glu Asn Pro Cys Cys
  1               5                  10                  15

Asp Ala Ala Thr Cys Lys Leu Arg Pro Gly Ala Gln Cys Ala Asp Gly
             20                  25                  30

Leu Cys Cys Asp Gln Cys Arg Phe Lys Lys Arg Thr Ile Cys Arg
         35                  40                  45

Arg Ala Arg Gly Asp Asn Pro Asp Asp Arg Cys Thr Gly Gln Ser Ala
 50                  55                  60

Asp Cys Pro Arg Asn Gly Leu Tyr Ser
 65                  70
```

<210> SEQ ID NO 7
<211> LENGTH: 62
<212> TYPE: PRT
<213> ORGANISM: Unknown
<220> FEATURE:
<223> OTHER INFORMATION: Trigramin

<400> SEQUENCE: 7

```
Glu Ala Gly Glu Asp Cys Asp Cys Gly Ser Pro Ser Asn Pro Cys Cys
  1               5                  10                  15

Asp Ala Ala Thr Cys Lys Leu Ile Pro Gly Ala Gln Cys Gly Glu Gly
             20                  25                  30

Leu Cys Cys Asp Gln Cys Ser Phe Ile Glu Glu Gly Thr Val Cys Arg
         35                  40                  45

Ile Ala Arg Gly Asp Asp Leu Asp Asp Tyr Cys Asn Gly Arg
 50                  55                  60
```

<210> SEQ ID NO 8
<211> LENGTH: 100
<212> TYPE: PRT
<213> ORGANISM: Artificial Sequence
<220> FEATURE:
<223> OTHER INFORMATION: VEGFR1 extracellular domain D2

<400> SEQUENCE: 8

```
Gly Arg Pro Phe Val Glu Met Tyr Ser Glu Ile Pro Glu Ile Ile His
  1               5                  10                  15

Met Thr Glu Gly Arg Glu Leu Val Ile Pro Cys Arg Val Thr Ser Pro
             20                  25                  30

Asn Ile Thr Val Thr Leu Lys Lys Phe Pro Leu Asp Thr Leu Ile Pro
         35                  40                  45

Asp Gly Lys Arg Ile Ile Trp Asp Ser Arg Lys Gly Phe Ile Ile Ser
 50                  55                  60

Asn Ala Thr Tyr Lys Glu Ile Gly Leu Leu Thr Cys Glu Ala Thr Val
 65                  70                  75                  80

Asn Gly His Leu Tyr Lys Thr Asn Tyr Leu Thr His Arg Gln Thr Asn
                 85                  90                  95

Thr Ile Ile Asp
```

```
                                100

<210> SEQ ID NO 9
<211> LENGTH: 102
<212> TYPE: PRT
<213> ORGANISM: Artificial Sequence
<220> FEATURE:
<223> OTHER INFORMATION: VEGFR2 extracellular domain D3

<400> SEQUENCE: 9

Val Val Leu Ser Pro Ser His Gly Ile Glu Leu Ser Val Gly Glu Lys
1               5                   10                  15

Leu Val Leu Asn Cys Thr Ala Arg Thr Glu Leu Asn Val Gly Ile Asp
            20                  25                  30

Phe Asn Trp Glu Tyr Pro Ser Ser Lys His Gln His Lys Lys Leu Val
        35                  40                  45

Asn Arg Asp Leu Lys Thr Gln Ser Gly Ser Glu Met Lys Lys Phe Leu
    50                  55                  60

Ser Thr Leu Thr Ile Asp Gly Val Thr Arg Ser Asp Gln Gly Leu Tyr
65                  70                  75                  80

Thr Cys Ala Ala Ser Ser Gly Leu Met Thr Lys Lys Asn Ser Thr Phe
                85                  90                  95

Val Arg Val His Glu Lys
            100

<210> SEQ ID NO 10
<211> LENGTH: 202
<212> TYPE: PRT
<213> ORGANISM: Artificial Sequence
<220> FEATURE:
<223> OTHER INFORMATION: VEGFR1 extracellular domain D2/VEGFR2
      extracellular domain D3

<400> SEQUENCE: 10

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190
```

-continued

```
<210> SEQ ID NO 11
<211> LENGTH: 299
<212> TYPE: PRT
<213> ORGANISM: Artificial Sequence
<220> FEATURE:
<223> OTHER INFORMATION: PDGFR-beta extracellular domains D1-D3

<400> SEQUENCE: 11
```

Asn Ser Thr Phe Val Arg Val His Glu Lys
        195                 200

Gln Gly Leu Val Val Thr Pro Pro Gly Pro Glu Leu Val Leu Asn Val
1               5                  10                  15

Ser Ser Thr Phe Val Leu Thr Cys Ser Gly Ser Ala Pro Val Val Trp
            20                  25                  30

Glu Arg Met Ser Gln Glu Pro Pro Gln Glu Met Ala Lys Ala Gln Asp
        35                  40                  45

Gly Thr Phe Ser Ser Val Leu Thr Leu Thr Asn Leu Thr Gly Leu Asp
    50                  55                  60

Thr Gly Glu Tyr Phe Cys Thr His Asn Asp Ser Arg Gly Leu Glu Thr
65                  70                  75                  80

Asp Glu Arg Lys Arg Leu Tyr Ile Phe Val Pro Asp Pro Thr Val Gly
                85                  90                  95

Phe Leu Pro Asn Asp Ala Glu Glu Leu Phe Ile Phe Leu Thr Glu Ile
            100                 105                 110

Thr Glu Ile Thr Ile Pro Cys Arg Val Thr Asp Pro Gln Leu Val Val
        115                 120                 125

Thr Leu His Glu Lys Lys Gly Asp Val Ala Leu Pro Val Pro Tyr Asp
    130                 135                 140

His Gln Arg Gly Phe Phe Gly Ile Phe Glu Asp Arg Ser Tyr Ile Cys
145                 150                 155                 160

Lys Thr Thr Ile Gly Asp Arg Glu Val Asp Ser Asp Ala Tyr Tyr Val
                165                 170                 175

Tyr Arg Leu Gln Val Ser Ser Ile Asn Val Ser Val Asn Ala Val Gln
            180                 185                 190

Thr Val Val Arg Gln Gly Glu Asn Ile Thr Leu Met Cys Ile Val Ile
        195                 200                 205

Gly Asn Glu Val Val Asn Phe Glu Trp Thr Tyr Pro Arg Lys Glu Ser
    210                 215                 220

Gly Arg Leu Val Glu Pro Val Thr Asp Phe Leu Leu Asp Met Pro Tyr
225                 230                 235                 240

His Ile Arg Ser Ile Leu His Ile Pro Ser Ala Glu Leu Glu Asp Ser
                245                 250                 255

Gly Thr Tyr Thr Cys Asn Val Thr Glu Ser Val Asn Asp His Gln Asp
            260                 265                 270

Glu Lys Ala Ile Asn Ile Thr Val Val Glu Ser Gly Tyr Val Arg Leu
        275                 280                 285

Leu Gly Glu Val Gly Thr Leu Gln Phe Ala Glu
    290                 295

```
<210> SEQ ID NO 12
<211> LENGTH: 70
<212> TYPE: PRT
<213> ORGANISM: Artificial Sequence
<220> FEATURE:
<223> OTHER INFORMATION: Rhodostomin variant KG-WN
```

```
<400> SEQUENCE: 12

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Arg Trp Asn Asp Leu
65                   70

<210> SEQ ID NO 13
<211> LENGTH: 68
<212> TYPE: PRT
<213> ORGANISM: Artificial Sequence
<220> FEATURE:
<223> OTHER INFORMATION: Rhodostomin variant KG

<400> SEQUENCE: 13

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Gly
        35                  40                  45

Arg Gly Asp Asn Pro Asp Asp Arg Cys Thr Gly Gln Ser Ala Asp Cys
    50                  55                  60

Pro Arg Tyr His
65

<210> SEQ ID NO 14
<211> LENGTH: 68
<212> TYPE: PRT
<213> ORGANISM: Artificial Sequence
<220> FEATURE:
<223> OTHER INFORMATION: Rhodostomin variant KA

<400> SEQUENCE: 14

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
            20                  25                  30

Cys Glu Gln Cys Lys Phe Lys Lys Ala Arg Thr Ile Cys Ala Arg Ala
        35                  40                  45

Arg Gly Asp Asn Pro Asp Asp Arg Cys Thr Gly Gln Ser Ala Asp Cys
    50                  55                  60

Pro Arg Tyr His
65

<210> SEQ ID NO 15
<211> LENGTH: 517
<212> TYPE: PRT
<213> ORGANISM: Artificial Sequence
<220> FEATURE:
<223> OTHER INFORMATION: Fusion of VEGFR1 D2/VEGFR2 D3 and Rhodostomin
      variant KG-WN

<400> SEQUENCE: 15

Gly Arg Pro Phe Val Glu Met Tyr Ser Glu Ile Pro Glu Ile Ile His
```

-continued

```
1               5                   10                  15
Met Thr Glu Gly Arg Glu Leu Val Ile Pro Cys Arg Val Thr Ser Pro
                20                  25                  30
Asn Ile Thr Val Thr Leu Lys Lys Phe Pro Leu Asp Thr Leu Ile Pro
                35                  40                  45
Asp Gly Lys Arg Ile Ile Trp Asp Ser Arg Lys Gly Phe Ile Ile Ser
    50                  55                  60
Asn Ala Thr Tyr Lys Glu Ile Gly Leu Leu Thr Cys Glu Ala Thr Val
65                  70                  75                  80
Asn Gly His Leu Tyr Lys Thr Asn Tyr Leu Thr His Arg Gln Thr Asn
                85                  90                  95
Thr Ile Ile Asp Val Val Leu Ser Pro Ser His Gly Ile Glu Leu Ser
                100                 105                 110
Val Gly Glu Lys Leu Val Leu Asn Cys Thr Ala Arg Thr Glu Leu Asn
                115                 120                 125
Val Gly Ile Asp Phe Asn Trp Glu Tyr Pro Ser Ser Lys His Gln His
    130                 135                 140
Lys Lys Leu Val Asn Arg Asp Leu Lys Thr Gln Ser Gly Ser Glu Met
145                 150                 155                 160
Lys Lys Phe Leu Ser Thr Leu Thr Ile Asp Gly Val Thr Arg Ser Asp
                165                 170                 175
Gln Gly Leu Tyr Thr Cys Ala Ala Ser Ser Gly Leu Met Thr Lys Lys
                180                 185                 190
Asn Ser Thr Phe Val Arg Val His Glu Lys Gly Pro Gly Asp Lys Thr
                195                 200                 205
His Thr Cys Pro Pro Cys Pro Ala Pro Glu Leu Leu Gly Gly Pro Ser
    210                 215                 220
Val Phe Leu Phe Pro Pro Lys Pro Lys Asp Thr Leu Met Ile Ser Arg
225                 230                 235                 240
Thr Pro Glu Val Thr Cys Val Val Val Asp Val Ser His Glu Asp Pro
                245                 250                 255
Glu Val Lys Phe Asn Trp Tyr Val Asp Gly Val Glu Val His Asn Ala
                260                 265                 270
Lys Thr Lys Pro Arg Glu Glu Gln Tyr Asn Ser Thr Tyr Arg Val Val
                275                 280                 285
Ser Val Leu Thr Val Leu His Gln Asp Trp Leu Asn Gly Lys Glu Tyr
    290                 295                 300
Lys Cys Lys Val Ser Asn Lys Ala Leu Pro Ala Pro Ile Glu Lys Thr
305                 310                 315                 320
Ile Ser Lys Ala Lys Gly Gln Pro Arg Glu Pro Gln Val Tyr Thr Leu
                325                 330                 335
Pro Pro Ser Arg Asp Glu Leu Thr Lys Asn Gln Val Ser Leu Thr Cys
                340                 345                 350
Leu Val Lys Gly Phe Tyr Pro Ser Asp Ile Ala Val Glu Trp Glu Ser
                355                 360                 365
Asn Gly Gln Pro Glu Asn Asn Tyr Lys Thr Thr Pro Pro Val Leu Asp
    370                 375                 380
Ser Asp Gly Ser Phe Phe Leu Tyr Ser Lys Leu Thr Val Asp Lys Ser
385                 390                 395                 400
Arg Trp Gln Gln Gly Asn Val Phe Ser Cys Ser Val Met His Glu Ala
                405                 410                 415
Leu His Asn His Tyr Thr Gln Lys Ser Leu Ser Leu Ser Pro Gly Lys
                420                 425                 430
```

Gly Gly Gly Gly Ser Gly Gly Gly Ser Gly Gly Gly Ser Gly
            435                 440                 445

Lys Glu Cys Asp Cys Ser Ser Pro Glu Asn Pro Cys Asp Ala Ala
450                 455                 460

Thr Cys Lys Leu Arg Pro Gly Ala Gln Cys Glu Gly Leu Cys Cys
465                 470                 475                 480

Glu Gln Cys Lys Phe Lys Lys Ala Arg Thr Ile Cys Ala Arg Gly
                485                 490                 495

Gly Asp Asn Pro Asp Asp Arg Cys Thr Gly Gln Ser Ala Asp Cys Pro
            500                 505                 510

Arg Trp Asn Asp Leu
            515

<210> SEQ ID NO 16
<211> LENGTH: 516
<212> TYPE: PRT
<213> ORGANISM: Artificial Sequence
<220> FEATURE:
<223> OTHER INFORMATION: Fusion of VEGFR1 D2/VEGFR2 D3 and Rhodostomin
      variant KG

<400> SEQUENCE: 16

Ser Gly Gly Arg Pro Phe Val Glu Met Tyr Ser Glu Ile Pro Glu Ile
1 5 10 15

Ile His Met Thr Glu Gly Arg Glu Leu Val Ile Pro Cys Arg Val Thr
20 25 30

Ser Pro Asn Ile Thr Val Thr Leu Lys Lys Phe Pro Leu Asp Thr Leu
35 40 45

Ile Pro Asp Gly Lys Arg Ile Ile Trp Asp Ser Arg Lys Gly Phe Ile
50 55 60

Ile Ser Asn Ala Thr Tyr Lys Glu Ile Gly Leu Leu Thr Cys Glu Ala
65 70 75 80

Thr Val Asn Gly His Leu Tyr Lys Thr Asn Tyr Leu Thr His Arg Gln
85 90 95

Thr Asn Thr Ile Ile Asp Val Val Leu Ser Pro Ser His Gly Ile Glu
100 105 110

Leu Ser Val Gly Glu Lys Leu Val Leu Asn Cys Thr Ala Arg Thr Glu
115 120 125

Leu Asn Val Gly Ile Asp Phe Asn Trp Glu Tyr Pro Ser Ser Lys His
130 135 140

Gln His Lys Lys Leu Val Asn Arg Asp Leu Lys Thr Gln Ser Gly Ser
145 150 155 160

Glu Met Lys Lys Phe Leu Ser Thr Leu Thr Ile Asp Gly Val Thr Arg
165 170 175

Ser Asp Gln Gly Leu Tyr Thr Cys Ala Ala Ser Ser Gly Leu Met Thr
180 185 190

Lys Lys Asn Ser Thr Phe Val Arg Val His Glu Lys Gly Pro Gly Asp
195 200 205

Lys Thr His Thr Cys Pro Pro Cys Pro Ala Pro Glu Leu Leu Gly Gly
210 215 220

Pro Ser Val Phe Leu Phe Pro Pro Lys Pro Lys Asp Thr Leu Met Ile
225 230 235 240

Ser Arg Thr Pro Glu Val Thr Cys Val Val Val Asp Val Ser His Glu
245 250 255

Asp Pro Glu Val Lys Phe Asn Trp Tyr Val Asp Gly Val Glu Val His

```
            260                 265                 270
Asn Ala Lys Thr Lys Pro Arg Glu Glu Gln Tyr Asn Ser Thr Tyr Arg
        275                 280                 285
Val Val Ser Val Leu Thr Val Leu His Gln Asp Trp Leu Asn Gly Lys
        290                 295                 300
Glu Tyr Lys Cys Lys Val Ser Asn Lys Ala Leu Pro Ala Pro Ile Glu
305                 310                 315                 320
Lys Thr Ile Ser Lys Ala Lys Gly Gln Pro Arg Glu Pro Gln Val Tyr
                325                 330                 335
Thr Leu Pro Pro Ser Arg Asp Glu Leu Thr Lys Asn Gln Val Ser Leu
            340                 345                 350
Thr Cys Leu Val Lys Gly Phe Tyr Pro Ser Asp Ile Ala Val Glu Trp
        355                 360                 365
Glu Ser Asn Gly Gln Pro Glu Asn Asn Tyr Lys Thr Thr Pro Pro Val
        370                 375                 380
Leu Asp Ser Asp Gly Ser Phe Phe Leu Tyr Ser Lys Leu Thr Val Asp
385                 390                 395                 400
Lys Ser Arg Trp Gln Gln Gly Asn Val Phe Ser Cys Ser Val Met His
                405                 410                 415
Glu Ala Leu His Asn His Tyr Thr Gln Lys Ser Leu Ser Leu Ser Pro
            420                 425                 430
Gly Gly Gly Gly Gly Ser Gly Gly Gly Gly Ser Gly Gly Gly Gly Ser
        435                 440                 445
Gly Lys Glu Cys Asp Cys Ser Ser Pro Glu Asn Pro Cys Cys Asp Ala
        450                 455                 460
Ala Thr Cys Lys Leu Arg Pro Gly Ala Gln Cys Gly Glu Gly Leu Cys
465                 470                 475                 480
Cys Glu Gln Cys Lys Phe Lys Lys Ala Arg Thr Ile Cys Ala Arg Gly
                485                 490                 495
Arg Gly Asp Asn Pro Asp Asp Arg Cys Thr Gly Gln Ser Ala Asp Cys
            500                 505                 510
Pro Arg Tyr His
        515

<210> SEQ ID NO 17
<211> LENGTH: 515
<212> TYPE: PRT
<213> ORGANISM: Artificial Sequence
<220> FEATURE:
<223> OTHER INFORMATION: Fusion of VEGFR1 D2/VEGFR2 D3 and Rhodostomin
      variant KA

<400> SEQUENCE: 17

Gly Arg Pro Phe Val Glu Met Tyr Ser Glu Ile Pro Glu Ile Ile His
1               5                   10                  15
Met Thr Glu Gly Arg Glu Leu Val Ile Pro Cys Arg Val Thr Ser Pro
            20                  25                  30
Asn Ile Thr Val Thr Leu Lys Lys Phe Pro Leu Asp Thr Leu Ile Pro
        35                  40                  45
Asp Gly Lys Arg Ile Ile Trp Asp Ser Arg Lys Gly Phe Ile Ile Ser
    50                  55                  60
Asn Ala Thr Tyr Lys Glu Ile Gly Leu Leu Thr Cys Glu Ala Thr Val
65                  70                  75                  80
Asn Gly His Leu Tyr Lys Thr Asn Tyr Leu Thr His Arg Gln Thr Asn
                85                  90                  95
```

```
Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Gly Pro Gly Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Lys
            420                 425                 430

Gly Gly Gly Gly Ser Gly Gly Gly Ser Gly Gly Gly Ser Gly
        435                 440                 445

Lys Glu Cys Asp Cys Ser Ser Pro Glu Asn Pro Cys Cys Asp Ala Ala
    450                 455                 460

Thr Cys Lys Leu Arg Pro Gly Ala Gln Cys Gly Glu Gly Leu Cys Cys
465                 470                 475                 480

Glu Gln Cys Lys Phe Lys Lys Ala Arg Thr Ile Cys Ala Arg Ala Arg
                485                 490                 495

Gly Asp Asn Pro Asp Asp Arg Cys Thr Gly Gln Ser Ala Asp Cys Pro
            500                 505                 510

Arg Tyr His
```

-continued

```
              515
```

<210> SEQ ID NO 18
<211> LENGTH: 514
<212> TYPE: PRT
<213> ORGANISM: Artificial Sequence
<220> FEATURE:
<223> OTHER INFORMATION: Fusion of Eylea and Rhodostomin variant KG

<400> SEQUENCE: 18

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser

```
                355             360             365
Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly Gly
            420                 425                 430

Gly Gly Gly Ser Gly Gly Gly Ser Gly Gly Gly Gly Ser Gly Lys
        435                 440                 445

Glu Cys Asp Cys Ser Ser Pro Glu Asn Pro Cys Cys Asp Ala Ala Thr
    450                 455                 460

Cys Lys Leu Arg Pro Gly Ala Gln Cys Gly Glu Gly Leu Cys Cys Glu
465                 470                 475                 480

Gln Cys Lys Phe Lys Lys Ala Arg Thr Ile Cys Ala Arg Gly Arg Gly
                485                 490                 495

Asp Asn Pro Asp Asp Arg Cys Thr Gly Gln Ser Ala Asp Cys Pro Arg
            500                 505                 510

Tyr His

<210> SEQ ID NO 19
<211> LENGTH: 1551
<212> TYPE: DNA
<213> ORGANISM: Artificial Sequence
<220> FEATURE:
<223> OTHER INFORMATION: nucleotide sequence of fusion protein of SEQ ID
      NO: 16

<400> SEQUENCE: 19
agcggcggaa ggcctttcgt cgagatgtac agcgagatcc ccagagatcat tcacatgacc        60 gaaggcaggg agctcgtgat cccttgcagg gtcacatccc caacatcac cgtcaccctc         120 aagaagttcc ccctggatac cctcatcccc gacggcaagc ggatcatttg ggatagccgg        180
aagggcttca tcatctccaa cgctacctac aaagaaattg gactgctgac ctgcgaggct        240
accgtcaacg gccacctcta taagaccaac tacctgaccc acaggcagac caataccatc        300
atcgatgtgg tcctcagccc cagccacgga atcgaactgt ccgtgggcga aagctggtc         360 ctgaactgta cagccaggac agaactcaac gtgggcatcg acttcaactg ggagtaccct        420
agctccaagc accagcacaa gaagctggtc aacgggacc tgaagaccca gtccggctcc         480
gaaatgaaga agttcctgtc caccctcacc atcgatggag tcacccggag cgatcaggga        540
ctgtatacct gcgccgcctc ctccggcctg atgacaaaga gaacagcac cttcgtgcgg         600 gtgcacgaga aaggccccgg cgacaagaca cacacctgcc ctccctgccc cgcccccgag        660
ctgctcgggg gacccagcgt gttcctgttc ccccctaagc ccaaggacac cctcatgatc        720
agcaggaccc ctgaggtgac atgcgtcgtc gtggacgtga gccatgaaga ccccgaggtg        780
aagttcaact ggtatgtgga cggcgtcgag gtgcataacg ccaagaccaa accccgggag        840
gagcaataca acagcacata cagggtggtg tccgtgctga ccgtcctgca ccaggattgg        900
ctgaacggca agagtataa gtgcaaggtg agcaacaaag ccctgccccgc tcccatcgag        960 aagacaatct ccaaggccaa gggccaaccc agggagcctc aggtgtacac actgcctcct       1020
tcccgggacg agctgacaaa aaaccaagtg agcctgacct gctcgtcaa gggcttctac       1080 ccttccgata tcgccgtgga gtgggagtcc aacggccagc tgagaacaa ctacaagacc       1140
```

```
accccteccg tgctcgattc cgacggctcc ttcttcctct acagcaagct cacagtggac    1200
aaatcccggt ggcagcaggg caatgtgttc agctgttccg tgatgcacga ggccctccac    1260
aatcactaca cccagaagag cctgtccctg tcccccggcg gaggcggcgg ctccggcgga    1320
ggcggctccg gcggcggcgg atccggaaaa gagtgcgatt gcagctcccc cgagaacccc    1380
tgctgcgatg ccgctacatg caaactgcgg cctggagccc agtgtggaga aggcctgtgc    1440
tgcgagcagt gcaagttcaa gaaggcccgg accatttgtg ctaggggccg gggagacaac    1500
cctgacgatc ggtgcaccgg ccaaagcgct gactgtcccc ggtaccactg a             1551
```

<210> SEQ ID NO 20
<211> LENGTH: 19
<212> TYPE: PRT
<213> ORGANISM: Artificial Sequence
<220> FEATURE:
<223> OTHER INFORMATION: A Signal Peptide

<400> SEQUENCE: 20

Met Ala Trp Ala Leu Leu Leu Thr Leu Leu Thr Arg Asp Thr Gly
1               5                   10                  15

Ser Trp Ala

<210> SEQ ID NO 21
<211> LENGTH: 57
<212> TYPE: DNA
<213> ORGANISM: Artificial Sequence
<220> FEATURE:
<223> OTHER INFORMATION: Nucleotide Sequence of a Signal Peptide

<400> SEQUENCE: 21
atggcctggg ctctcctgct gctgaccctg ctgacacggg acacaggatc ctgggcc       57

<210> SEQ ID NO 22
<211> LENGTH: 26
<212> TYPE: PRT
<213> ORGANISM: Artificial Sequence
<220> FEATURE:
<223> OTHER INFORMATION: Signaling Peptide of Fusion Protein of SEQ ID
      NO: 18

<400> SEQUENCE: 22

Met Val Ser Tyr Trp Asp Thr Gly Val Leu Leu Cys Ala Leu Leu Ser
1               5                   10                  15

Cys Leu Leu Leu Thr Gly Ser Ser Ser Gly
            20                  25

<210> SEQ ID NO 23
<211> LENGTH: 431
<212> TYPE: PRT
<213> ORGANISM: Artificial Sequence
<220> FEATURE:
<223> OTHER INFORMATION: VEGFR1 domain D2/VEGFR2 domain D3 fused to IgG1
      Fc

<400> SEQUENCE: 23

Asp Thr Gly Arg Pro Phe Val Glu Met Tyr Ser Glu Ile Pro Glu Ile
1               5                   10                  15

Ile His Met Thr Glu Gly Arg Glu Leu Val Ile Pro Cys Arg Val Thr
                20                  25                  30

Ser Pro Asn Ile Thr Val Thr Leu Lys Lys Phe Pro Leu Asp Thr Leu
        35                  40                  45

Ile Pro Asp Gly Lys Arg Ile Ile Trp Asp Ser Arg Lys Gly Phe Ile
 50                  55                  60

Ile Ser Asn Ala Thr Tyr Lys Glu Ile Gly Leu Leu Thr Cys Glu Ala
 65                  70                  75                  80

Thr Val Asn Gly His Leu Tyr Lys Thr Asn Tyr Leu Thr His Arg Gln
                 85                  90                  95

Thr Asn Thr Ile Ile Asp Val Val Leu Ser Pro Ser His Gly Ile Glu
            100                 105                 110

Leu Ser Val Gly Glu Lys Leu Val Leu Asn Cys Thr Ala Arg Thr Glu
                115                 120                 125

Leu Asn Val Gly Ile Asp Phe Asn Trp Glu Tyr Pro Ser Ser Lys His
130                 135                 140

Gln His Lys Lys Leu Val Asn Arg Asp Leu Lys Thr Gln Ser Gly Ser
145                 150                 155                 160

Glu Met Lys Lys Phe Leu Ser Thr Leu Thr Ile Asp Gly Val Thr Arg
                165                 170                 175

Ser Asp Gln Gly Leu Tyr Thr Cys Ala Ala Ser Ser Gly Leu Met Thr
                180                 185                 190

Lys Lys Asn Ser Thr Phe Val Arg Val His Glu Lys Asp Lys Thr His
                195                 200                 205

Thr Cys Pro Pro Cys Pro Ala Pro Glu Leu Leu Gly Gly Pro Ser Val
210                 215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser His Glu Asp Pro Glu
                245                 250                 255

Val Lys Phe Asn Trp Tyr Val Asp Gly Val Glu Val His Asn Ala Lys
                260                 265                 270

Thr Lys Pro Arg Glu Glu Gln Tyr Asn Ser Thr Tyr Arg Val Val Ser
                275                 280                 285

Val Leu Thr Val Leu His Gln Asp Trp Leu Asn Gly Lys Glu Tyr Lys
                290                 295                 300

Cys Lys Val Ser Asn Lys Ala Leu Pro Ala Pro Ile Glu Lys Thr Ile
305                 310                 315                 320

Ser Lys Ala Lys Gly Gln Pro Arg Glu Pro Gln Val Tyr Thr Leu Pro
                325                 330                 335

Pro Ser Arg Asp Glu Leu Thr Lys Asn Gln Val Ser Leu Thr Cys Leu
                340                 345                 350

Val Lys Gly Phe Tyr Pro Ser Asp Ile Ala Val Glu Trp Glu Ser Asn
                355                 360                 365

Gly Gln Pro Glu Asn Asn Tyr Lys Thr Thr Pro Pro Val Leu Asp Ser
370                 375                 380

Asp Gly Ser Phe Phe Leu Tyr Ser Lys Leu Thr Val Asp Lys Ser Arg
385                 390                 395                 400

Trp Gln Gln Gly Asn Val Phe Ser Cys Ser Val Met His Glu Ala Leu
                405                 410                 415

His Asn His Tyr Thr Gln Lys Ser Leu Ser Leu Ser Pro Gly Lys
                420                 425                 430

<210> SEQ ID NO 24
<211> LENGTH: 8
<212> TYPE: PRT
<213> ORGANISM: Artificial Sequence
<220> FEATURE:
<223> OTHER INFORMATION: mutant RGD

```
<400> SEQUENCE: 24

Arg Ile Ala Arg Gly Asp Asn Pro
1               5

<210> SEQ ID NO 25
<211> LENGTH: 8
<212> TYPE: PRT
<213> ORGANISM: Artificial Sequence
<220> FEATURE:
<223> OTHER INFORMATION: mutant RGD

<400> SEQUENCE: 25

Arg Arg Ala Arg Gly Asp Asn Pro
1               5

<210> SEQ ID NO 26
<211> LENGTH: 8
<212> TYPE: PRT
<213> ORGANISM: Artificial Sequence
<220> FEATURE:
<223> OTHER INFORMATION: mutant RGD

<400> SEQUENCE: 26

Ala Arg Gly Arg Gly Asp Asn Pro
1               5

<210> SEQ ID NO 27
<211> LENGTH: 8
<212> TYPE: PRT
<213> ORGANISM: Artificial Sequence
<220> FEATURE:
<223> OTHER INFORMATION: mutant RGD loop sequence

<400> SEQUENCE: 27

Ala Arg Gly Arg Gly Asp Asp Leu
1               5

<210> SEQ ID NO 28
<211> LENGTH: 8
<212> TYPE: PRT
<213> ORGANISM: Artificial Sequence
<220> FEATURE:
<223> OTHER INFORMATION: mutant RGD loop sequence

<400> SEQUENCE: 28

Ala Arg Ala Arg Gly Asp Asn Pro
1               5

<210> SEQ ID NO 29
<211> LENGTH: 7
<212> TYPE: PRT
<213> ORGANISM: Artificial Sequence
<220> FEATURE:
<223> OTHER INFORMATION: mutant linker

<400> SEQUENCE: 29

Lys Lys Lys Arg Thr Ile Cys
1               5

<210> SEQ ID NO 30
<211> LENGTH: 7
<212> TYPE: PRT
<213> ORGANISM: Artificial Sequence
<220> FEATURE:
<223> OTHER INFORMATION: mutant linker
```

```
<400> SEQUENCE: 30

Met Lys Lys Gly Thr Ile Cys
1               5

<210> SEQ ID NO 31
<211> LENGTH: 7
<212> TYPE: PRT
<213> ORGANISM: Artificial Sequence
<220> FEATURE:
<223> OTHER INFORMATION: mutant linker

<400> SEQUENCE: 31

Ile Glu Glu Gly Thr Ile Cys
1               5

<210> SEQ ID NO 32
<211> LENGTH: 7
<212> TYPE: PRT
<213> ORGANISM: Artificial Sequence
<220> FEATURE:
<223> OTHER INFORMATION: mutant linker

<400> SEQUENCE: 32

Lys Gly Ala Gly Lys Ile Cys
1               5

<210> SEQ ID NO 33
<211> LENGTH: 7
<212> TYPE: PRT
<213> ORGANISM: Artificial Sequence
<220> FEATURE:
<223> OTHER INFORMATION: mutant linker

<400> SEQUENCE: 33

Leu Lys Glu Gly Thr Ile Cys
1               5

<210> SEQ ID NO 34
<211> LENGTH: 7
<212> TYPE: PRT
<213> ORGANISM: Artificial Sequence
<220> FEATURE:
<223> OTHER INFORMATION: mutant linker

<400> SEQUENCE: 34

Ala Lys Lys Arg Thr Ile Cys
1               5

<210> SEQ ID NO 35
<211> LENGTH: 7
<212> TYPE: PRT
<213> ORGANISM: Artificial Sequence
<220> FEATURE:
<223> OTHER INFORMATION: mutant linker

<400> SEQUENCE: 35

Lys Ala Lys Arg Thr Ile Cys
1               5

<210> SEQ ID NO 36
<211> LENGTH: 7
<212> TYPE: PRT
<213> ORGANISM: Artificial Sequence
<220> FEATURE:
<223> OTHER INFORMATION: mutant linker

<400> SEQUENCE: 36
```

```
Lys Lys Ala Arg Thr Ile Cys
1               5

<210> SEQ ID NO 37
<211> LENGTH: 7
<212> TYPE: PRT
<213> ORGANISM: Artificial Sequence
<220> FEATURE:
<223> OTHER INFORMATION: mutant linker

<400> SEQUENCE: 37

Lys Lys Lys Ala Thr Ile Cys
1               5

<210> SEQ ID NO 38
<211> LENGTH: 7
<212> TYPE: PRT
<213> ORGANISM: Artificial Sequence
<220> FEATURE:
<223> OTHER INFORMATION: mutant linker

<400> SEQUENCE: 38

Lys Lys Lys Arg Ala Ile Cys
1               5

<210> SEQ ID NO 39
<211> LENGTH: 7
<212> TYPE: PRT
<213> ORGANISM: Artificial Sequence
<220> FEATURE:
<223> OTHER INFORMATION: mutant linker

<400> SEQUENCE: 39

Lys Ala Lys Arg Ala Ile Cys
1               5

<210> SEQ ID NO 40
<211> LENGTH: 7
<212> TYPE: PRT
<213> ORGANISM: Artificial Sequence
<220> FEATURE:
<223> OTHER INFORMATION: mutant linker

<400> SEQUENCE: 40

Ser Lys Ala Gly Thr Ile Cys
1               5

<210> SEQ ID NO 41
<211> LENGTH: 7
<212> TYPE: PRT
<213> ORGANISM: Artificial Sequence
<220> FEATURE:
<223> OTHER INFORMATION: mutant linker

<400> SEQUENCE: 41

Lys Lys Lys Arg Thr Ile Cys
1               5

<210> SEQ ID NO 42
<211> LENGTH: 6
<212> TYPE: PRT
<213> ORGANISM: Artificial Sequence
<220> FEATURE:
<223> OTHER INFORMATION: mutant C-terminus

<400> SEQUENCE: 42
```

```
Pro Arg Trp Asn Asp Leu
1               5
```

\<210\> SEQ ID NO 43
\<211\> LENGTH: 7
\<212\> TYPE: PRT
\<213\> ORGANISM: Artificial Sequence
\<220\> FEATURE:
\<223\> OTHER INFORMATION: mutant C-terminus

\<400\> SEQUENCE: 43

```
Pro Arg Asn Gly Leu Tyr Gly
1               5
```

\<210\> SEQ ID NO 44
\<211\> LENGTH: 5
\<212\> TYPE: PRT
\<213\> ORGANISM: Artificial Sequence
\<220\> FEATURE:
\<223\> OTHER INFORMATION: mutant C-terminus

\<400\> SEQUENCE: 44

```
Pro Gly Leu Tyr Gly
1               5
```

\<210\> SEQ ID NO 45
\<211\> LENGTH: 5
\<212\> TYPE: PRT
\<213\> ORGANISM: Artificial Sequence
\<220\> FEATURE:
\<223\> OTHER INFORMATION: mutant C-terminus

\<400\> SEQUENCE: 45

```
Pro Asp Leu Tyr Gly
1               5
```

\<210\> SEQ ID NO 46
\<211\> LENGTH: 5
\<212\> TYPE: PRT
\<213\> ORGANISM: Artificial Sequence
\<220\> FEATURE:
\<223\> OTHER INFORMATION: mutant C-terminus

\<400\> SEQUENCE: 46

```
Pro Pro Leu Tyr Gly
1               5
```

\<210\> SEQ ID NO 47
\<211\> LENGTH: 5
\<212\> TYPE: PRT
\<213\> ORGANISM: Artificial Sequence
\<220\> FEATURE:
\<223\> OTHER INFORMATION: mutant C-terminus

\<400\> SEQUENCE: 47

```
Pro Arg Leu Tyr Gly
1               5
```

\<210\> SEQ ID NO 48
\<211\> LENGTH: 5
\<212\> TYPE: PRT
\<213\> ORGANISM: Artificial Sequence
\<220\> FEATURE:
\<223\> OTHER INFORMATION: mutant C-terminus

\<400\> SEQUENCE: 48

```
Pro Glu Leu Tyr Gly
```

```
1               5

<210> SEQ ID NO 49
<211> LENGTH: 5
<212> TYPE: PRT
<213> ORGANISM: Artificial Sequence
<220> FEATURE:
<223> OTHER INFORMATION: mutant C-terminus

<400> SEQUENCE: 49

Pro Tyr Leu Tyr Gly
1               5

<210> SEQ ID NO 50
<211> LENGTH: 5
<212> TYPE: PRT
<213> ORGANISM: Artificial Sequence
<220> FEATURE:
<223> OTHER INFORMATION: Mutant

<400> SEQUENCE: 50

Ser Arg Ala Gly Lys
1               5

<210> SEQ ID NO 51
<211> LENGTH: 5
<212> TYPE: PRT
<213> ORGANISM: Artificial Sequence
<220> FEATURE:
<223> OTHER INFORMATION: Mutant

<400> SEQUENCE: 51

Lys Lys Lys Arg Thr
1               5

<210> SEQ ID NO 52
<211> LENGTH: 5
<212> TYPE: PRT
<213> ORGANISM: Artificial Sequence
<220> FEATURE:
<223> OTHER INFORMATION: Mutant

<400> SEQUENCE: 52

Lys Lys Ala Arg Thr
1               5

<210> SEQ ID NO 53
<211> LENGTH: 5
<212> TYPE: PRT
<213> ORGANISM: Artificial Sequence
<220> FEATURE:
<223> OTHER INFORMATION: Mutant

<400> SEQUENCE: 53

Met Lys Lys Gly Thr
1               5

<210> SEQ ID NO 54
<211> LENGTH: 5
<212> TYPE: PRT
<213> ORGANISM: Artificial Sequence
<220> FEATURE:
<223> OTHER INFORMATION: Mutant

<400> SEQUENCE: 54

Ile Glu Glu Gly Thr
1               5
```

```
<210> SEQ ID NO 55
<211> LENGTH: 5
<212> TYPE: PRT
<213> ORGANISM: Artificial Sequence
<220> FEATURE:
<223> OTHER INFORMATION: Mutant

<400> SEQUENCE: 55

Leu Lys Glu Gly Thr
1               5

<210> SEQ ID NO 56
<211> LENGTH: 5
<212> TYPE: PRT
<213> ORGANISM: Artificial Sequence
<220> FEATURE:
<223> OTHER INFORMATION: Mutant

<400> SEQUENCE: 56

Ala Lys Lys Arg Thr
1               5

<210> SEQ ID NO 57
<211> LENGTH: 5
<212> TYPE: PRT
<213> ORGANISM: Artificial Sequence
<220> FEATURE:
<223> OTHER INFORMATION: Mutant

<400> SEQUENCE: 57

Lys Ala Lys Arg Thr
1               5

<210> SEQ ID NO 58
<211> LENGTH: 5
<212> TYPE: PRT
<213> ORGANISM: Artificial Sequence
<220> FEATURE:
<223> OTHER INFORMATION: Mutant

<400> SEQUENCE: 58

Lys Lys Ala Arg Thr
1               5

<210> SEQ ID NO 59
<211> LENGTH: 5
<212> TYPE: PRT
<213> ORGANISM: Artificial Sequence
<220> FEATURE:
<223> OTHER INFORMATION: Mutant

<400> SEQUENCE: 59

Lys Lys Lys Ala Thr
1               5

<210> SEQ ID NO 60
<211> LENGTH: 5
<212> TYPE: PRT
<213> ORGANISM: Artificial Sequence
<220> FEATURE:
<223> OTHER INFORMATION: Mutant

<400> SEQUENCE: 60

Lys Lys Lys Arg Ala
1               5
```

```
<210> SEQ ID NO 61
<211> LENGTH: 5
<212> TYPE: PRT
<213> ORGANISM: Artificial Sequence
<220> FEATURE:
<223> OTHER INFORMATION: Mutant

<400> SEQUENCE: 61

Lys Ala Lys Arg Ala
1               5

<210> SEQ ID NO 62
<211> LENGTH: 5
<212> TYPE: PRT
<213> ORGANISM: Artificial Sequence
<220> FEATURE:
<223> OTHER INFORMATION: Mutant

<400> SEQUENCE: 62

Ser Lys Ala Gly Thr
1               5

<210> SEQ ID NO 63
<211> LENGTH: 3
<212> TYPE: PRT
<213> ORGANISM: Artificial Sequence
<220> FEATURE:
<223> OTHER INFORMATION: Mutant

<400> SEQUENCE: 63

Arg Tyr His
1

<210> SEQ ID NO 64
<211> LENGTH: 4
<212> TYPE: PRT
<213> ORGANISM: Artificial Sequence
<220> FEATURE:
<223> OTHER INFORMATION: Mutant

<400> SEQUENCE: 64

Arg Asn Gly Leu
1

<210> SEQ ID NO 65
<211> LENGTH: 5
<212> TYPE: PRT
<213> ORGANISM: Artificial Sequence
<220> FEATURE:
<223> OTHER INFORMATION: Mutant

<400> SEQUENCE: 65

Arg Gly Leu Tyr Gly
1               5

<210> SEQ ID NO 66
<211> LENGTH: 4
<212> TYPE: PRT
<213> ORGANISM: Artificial Sequence
<220> FEATURE:
<223> OTHER INFORMATION: Mutant

<400> SEQUENCE: 66

Arg Gly Leu Tyr
1
```

-continued

```
<210> SEQ ID NO 67
<211> LENGTH: 5
<212> TYPE: PRT
<213> ORGANISM: Artificial Sequence
<220> FEATURE:
<223> OTHER INFORMATION: Mutant

<400> SEQUENCE: 67

Arg Asp Leu Tyr Gly
1               5

<210> SEQ ID NO 68
<211> LENGTH: 4
<212> TYPE: PRT
<213> ORGANISM: Artificial Sequence
<220> FEATURE:
<223> OTHER INFORMATION: Mutant

<400> SEQUENCE: 68

Arg Asp Leu Tyr
1

<210> SEQ ID NO 69
<211> LENGTH: 6
<212> TYPE: PRT
<213> ORGANISM: Artificial Sequence
<220> FEATURE:
<223> OTHER INFORMATION: Mutant

<400> SEQUENCE: 69

Arg Asn Gly Leu Tyr Gly
1               5

<210> SEQ ID NO 70
<211> LENGTH: 6
<212> TYPE: PRT
<213> ORGANISM: Artificial Sequence
<220> FEATURE:
<223> OTHER INFORMATION: Mutant

<400> SEQUENCE: 70

Arg Asn Pro Trp Asn Gly
1               5
```